(12) United States Patent
Liu et al.

(10) Patent No.: US 11,710,249 B2
(45) Date of Patent: Jul. 25, 2023

(54) GENERATION OF THREE-DIMENSIONAL SCANS FOR INTRAOPERATIVE IMAGING

(71) Applicant: Unify Medical Inc., Westlake, OH (US)

(72) Inventors: Yang Liu, Westlake, OH (US); Maziyar Askari Karchegani, Coralville, IA (US)

(73) Assignee: Unify Medical, Inc., Cleveland, OH (US)

( * ) Notice: Subject to any disclaimer, the term of this patent is extended or adjusted under 35 U.S.C. 154(b) by 0 days.

(21) Appl. No.: 17/129,691

(22) Filed: Dec. 21, 2020

(65) Prior Publication Data

US 2021/0192763 A1 Jun. 24, 2021

Related U.S. Application Data

(60) Provisional application No. 63/040,816, filed on Jun. 18, 2020, provisional application No. 62/951,480, filed on Dec. 20, 2019.

(51) Int. Cl.
*G06T 7/593* (2017.01)
*H04N 13/239* (2018.01)
(Continued)

(52) U.S. Cl.
CPC ............. *G06T 7/593* (2017.01); *A61B 34/20* (2016.02); *G06T 7/33* (2017.01); *G06T 7/73* (2017.01); *H04N 13/239* (2018.05); *A61B 2034/2051* (2016.02); *A61B 2034/2055* (2016.02); *A61B 2034/2065* (2016.02);
(Continued)

(58) Field of Classification Search
CPC .. H04N 13/106; H04N 13/239; H04N 13/302; H04N 13/332; H04N 2013/0081; G06T 2207/10012; G06T 2207/20084; G06T 2207/30004; G06T 2207/30012; G06T 2207/30196; G06T 7/30; G06T 7/33; G06T 7/521; G06T 7/593; G06T 7/73; G06T 2207/3019; A61B 2034/2051;
(Continued)

(56) References Cited

U.S. PATENT DOCUMENTS 7,450,743 B2 11/2008 Sundar et al.
7,689,019 B2 3/2010 Boese et al.
(Continued)

*Primary Examiner* — Farzana Hossain
(74) *Attorney, Agent, or Firm* — Taft Stettinius & Hollister LLP

(57) ABSTRACT

A system for executing a three-dimensional (3D) intraoperative scan of a patient is disclosed. A 3D scanner controller projects the object points included onto a first image plane and the object points onto a second image plane. The 3D scanner controller determines first epipolar lines associated with the first image plane and second epipolar lines associated with the second image plane based on an epipolar plane that triangulates the object points included in the first 2D intraoperative image to the object points included in the second 2D intraoperative image. Each epipolar lines provides a depth of each object as projected onto the first image plane and the second image plane. The 3D scanner controller converts the first 2D intraoperative image and the second 2D intraoperative image to the 3D intraoperative scan of the patient based on the depth of each object point provided by each corresponding epipolar line.

6 Claims, 10 Drawing Sheets

(51) Int. Cl.
*G06T 7/33* (2017.01)
*G06T 7/73* (2017.01)
*A61B 34/20* (2016.01)
*H04N 13/00* (2018.01)

(52) U.S. Cl.
CPC ............... *G06T 2207/10012* (2013.01); *G06T 2207/30004* (2013.01); *H04N 2013/0081* (2013.01)

(58) Field of Classification Search
CPC .... A61B 2034/2055; A61B 2034/2065; A61B 2090/373; A61B 34/20; A61B 90/37
See application file for complete search history.

(56) References Cited

U.S. PATENT DOCUMENTS

| | | |
|---|---|---|
| 8,694,075 B2 | 4/2014 | Groszmann et al. |
| 8,705,829 B2 | 4/2014 | Frank et al. |
| 8,818,105 B2 | 8/2014 | Myronenko et al. |
| 9,105,092 B2 | 8/2015 | Lee et al. |
| 9,119,670 B2 | 9/2015 | Yang et al. |
| 9,513,113 B2 | 12/2016 | Yang et al. |
| 10,013,777 B2 | 7/2018 | Mariampillai et al. |
| 2018/0308263 A1 | 10/2018 | Mariampillai et al. |
| 2019/0038365 A1* | 2/2019 | Soper .................... A61B 34/10 |

* cited by examiner

GENERATION OF THREE-DIMENSIONAL SCANS FOR INTRAOPERATIVE IMAGING

CROSS-REFERENCE TO RELATED APPLICATION

This application claims the benefit of U.S. Provisional Application No. 62/951,480 filed on Dec. 20, 2019 and U.S. Provisional Application No. 63/040,816 filed on Jun. 18, 2020, which are incorporated herein by reference in their entirety.

TECHNICAL FIELD

Generally, the present invention relates to apparatuses, systems, and methods of surgical imaging, navigation and tracking. In particular, the present invention relates to systems and methods for performing 3D scanning, surgical imaging, tracking, image processing, computer vision, image registration, and display. More particularly, the present invention relates to an apparatus, system, and method for utilizing 3D scanning, intraoperative imaging, light source, tracking hardware, in combination with image processing and computer vision algorithms, to perform procedural guidance.

BACKGROUND OF THE INVENTION

Current surgical imaging and navigation hardware and software, such as those used in the spine and orthopedic fields, still fail to deliver robust procedure guidance, as desired by surgeons. There is a need for a system that can provide accurate guidance for surgical applications for hard tissues and soft tissues alike. There is a need for systems that is capable of being used in various applications such as surgery, therapeutic monitoring, and medical training. Furthermore, there is a need for an imaging system that combines augmented reality, real time imaging, procedure guidance, and decision support.

BRIEF DESCRIPTION OF THE DRAWINGS/FIGURES

Embodiments of the present disclosure are described with reference to the accompanying drawings. In the drawings, like reference numerals indicate identical or functionally similar elements. Additionally, the left most digit(s) of a reference number typically identifies the drawing in which the reference number first appears.

DETAILED DESCRIPTION OF THE INVENTION

Figure 1:
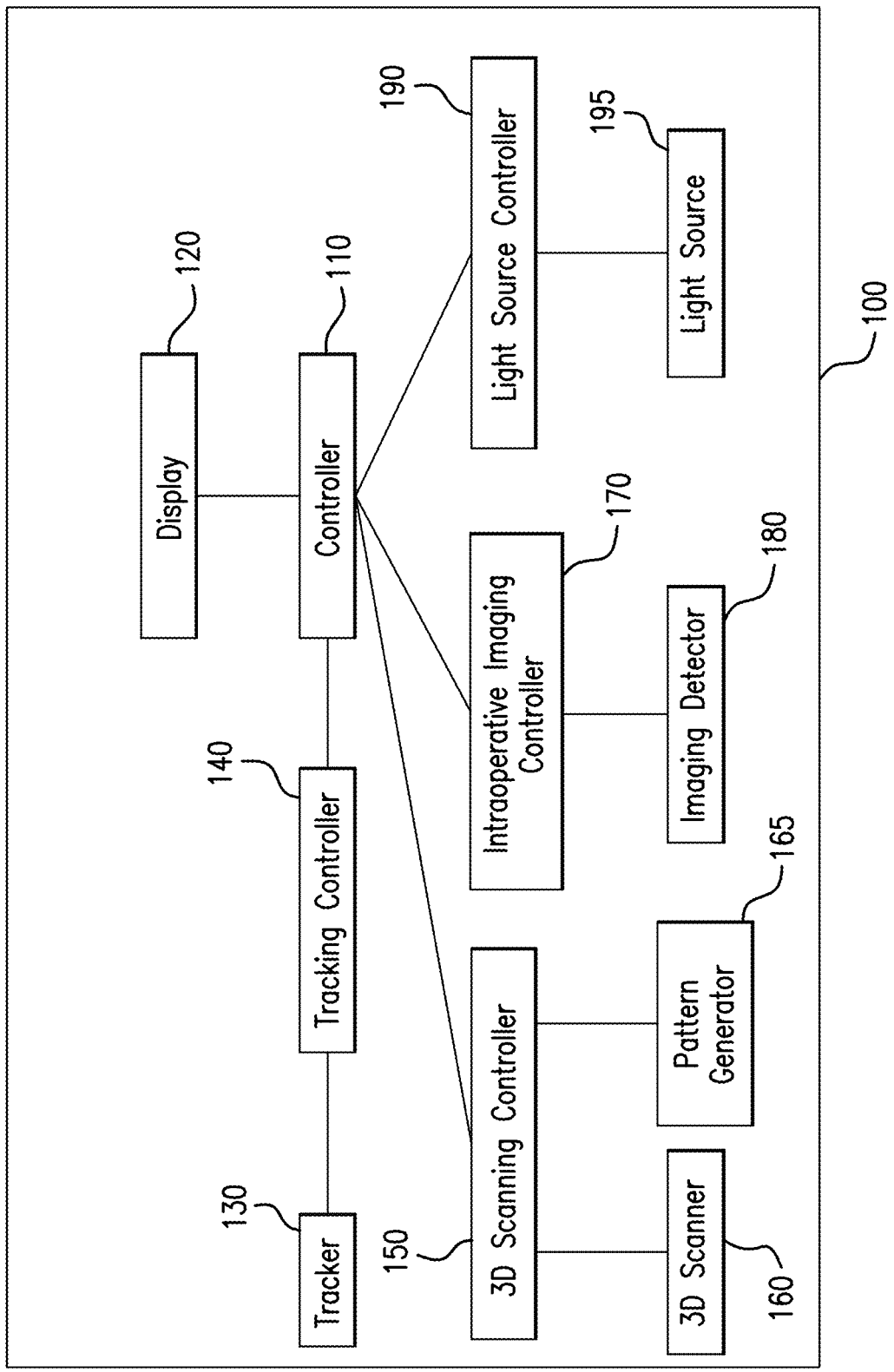
FIG. 1 illustrates a block diagram of a surgical imaging and navigation system.

A surgical imaging and navigation system 100 of the present invention is shown in FIG. 1. In one embodiment, the surgical imaging and navigation system 100 includes a display 120, a controller 110, a 3D scanning controller 150, a 3D scanner 160, an intraoperative imaging controller 170, an imaging detector 180, a light source controller 190, a light source 195, a tracking controller 140, and a tracker 130. The 3D scanning controller 150 controls the modes and properties of the 3D scanner 160. For instance, the size of the area of 3D scanning, the resolution of 3D scanning, the speed of 3D scanning, the timing of 3D scanning may be controlled by the 3D scanning controller 150. The intraoperative imaging controller 170 controls the modes and properties of imaging detector 180. For instance, the size of the area of intraoperative imaging, the resolution of intraoperative imaging, the speed of intraoperative imaging, the timing of intraoperative imaging, and the mode of intraoperative imaging may be controlled by the intraoperative imaging controller 170.

The light source controller 190 controls the modes and properties of light source. For instance, the size of the area of the light source 195 to shine on, the power of the light source 195, the wavelength of the light source 195, the frequency of the light source 195, the timing of the light source 195 may be controlled by the light source controller 190. The tracker 130 may track the surgical tools and other objects, via optical tracking, electromagnetic tracking, or a combination thereof. The tracking controller 140 controls how the tracker 130 tracks the surgical tools and other objects. The display 120 may display the surgical navigation information to the user. The controller 110 is in in operative communication with the 3D scanning controller 150, intraoperative imaging controller 170, light source controller 190, the tracking controller 140, and the display 120. The controller may run software such as image registration software or computer vision algorithms to enable surgical navigation. The display 120 may be display medical information to the user in 2D or 3D. For example, the display 120 may be a traditional 2D monitor or a head mounted display that may display images to the user in 3D. It should be appreciated the descriptions above are only one example how the surgical imaging and navigation system 100 may work.

With an exemplary system previously discussed, surgical imaging and navigation may be implemented to provide intraoperative guidance to surgeons and other medical professionals. The 3D scanner 160 may capture a 3D scan of an anatomy of a patient as controlled by the 3D scanning controller 150. The imaging detector 180 may capture at least one mode of an intraoperative image of a patient as controlled by the intraoperative imaging controller 170. The light source 195 may provide intraoperative illumination on the patient as controlled by the light source controller 190. The controller 110 may register the preoperative image data to the intraoperative 3D scan. The tracker 130 may track at least one entity in surgery as controlled by the tracking controller 140. The display 120 may display the surgical navigation information to the user.

3D Scanner with Epipolar Geometry

Figure 2:
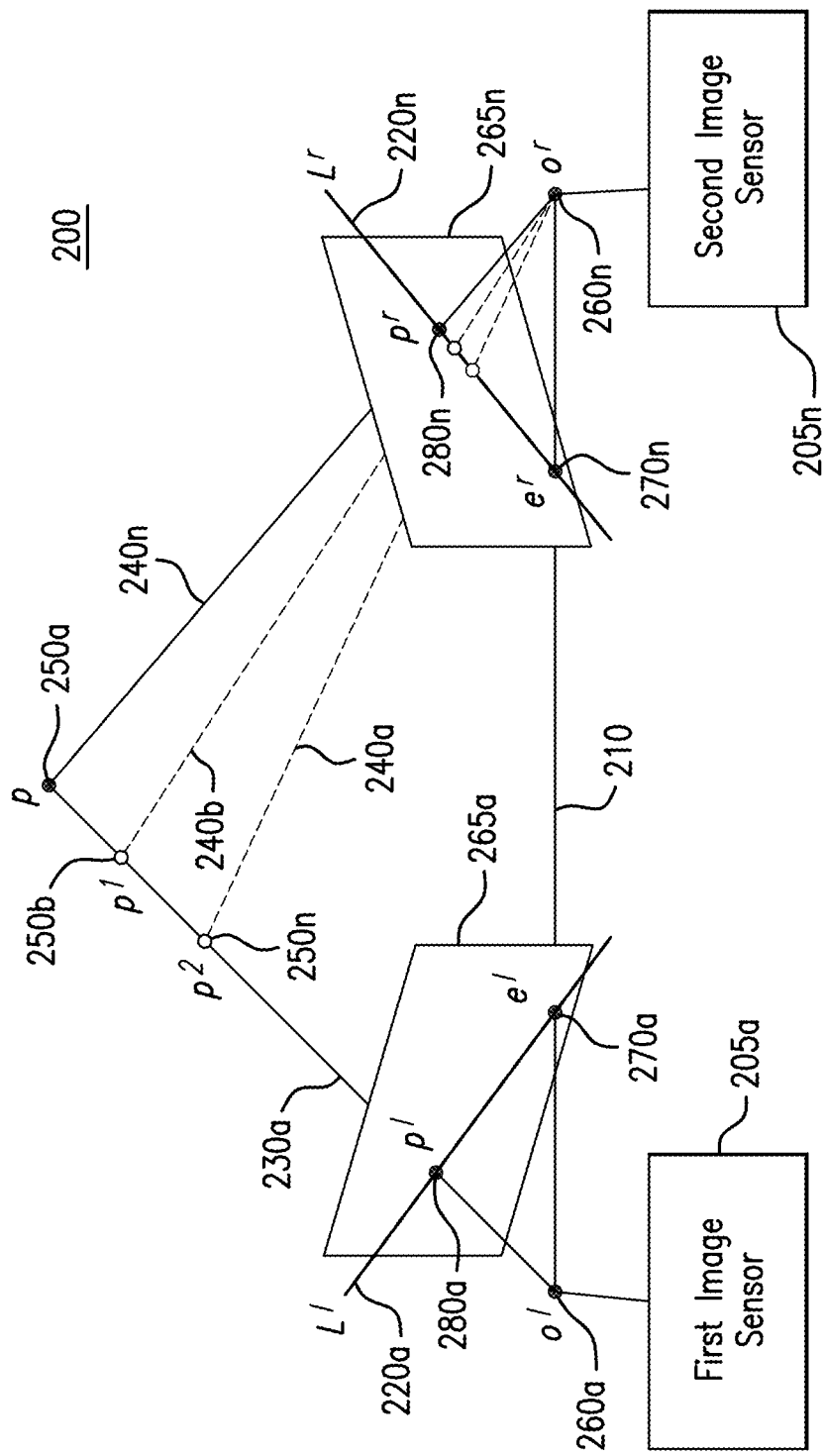
FIG. 2 is a schematic view of a 3D scanner epipolar geometry configuration where the 3D scanner implements epipolar geometry.

FIG. 1 illustrates a block diagram of the surgical imaging and navigation system 100 that may execute a 3D intraoperative scan of a patient to generate a plurality of intraoperative images of the patient that enables a surgeon to navigate a surgical operation on the patient. The 3D scanner 160 that includes a first image sensor 205a and a second image sensor 205n may capture a first two-dimensional (2D) intraoperative image 260a of a plurality of object points 250(a-n), where n is an integer equal to or greater than one and is associated with the patient via the first image sensor 205a and a second 2D intraoperative image 265n of the plurality of object points 250(a-n) via the second image sensor 205n. For example, FIG. 2 is a schematic view of a 3D scanner epipolar geometry configuration 200 where the 3D scanner 160 implements epipolar geometry.

The 3D scanning controller 150 may project the plurality of object points 250(a-n) included in the first 2D intraoperative image 260a onto a first image plane 265a associated with the first image sensor 205a and the plurality of object points 250(a-n) included in the second 2D intraoperative image 260n onto a second image plane 265n associated with the second image sensor 205n. The 3D scanning controller 150 may determine a plurality of first epipolar lines 220a associated with the first image plane 265a and a plurality of second epipolar lines 220n associated with the second image plane 265n based on an epipolar plane 210 that triangulates the plurality of object points 250(a-n) included in the first 2D intraoperative image 260a to the plurality of object points 250(a-n) included in the second 2D intraoperative image 260n. Each epipolar line 220(a-n) provides depth of each object point 250(a-n) as projected onto the first image plane 265a associated with the first image sensor 205a and the second image plane 265n associated with the second image sensor 205n. The 3D scanning controller 150 may convert the first 2D intraoperative image 260a and the second 2D intraoperative image 260n to the 3D intraoperative scan of the patient based on the depth of each object point 250(a-n) provided by each corresponding epipolar line 220(a-n).

The controller 110 may co-register pre-operative image data captured from at least one pre-operative image of the patient with intraoperative image data provided by the 3D intraoperative scan. The controller 110 may instruct the display 120 to display the co-registered pre-operative image data as captured by the at least one pre-operative image with the intraoperative image data provided by the 3D intraoperative scan as the surgeon navigates during the surgical operation.

The 3D scanner 160 may be controlled by the 3D scanning controller 150 to perform a 3D scan of the patient during the surgery. In one embodiment, the 3D scanner 160 includes two or more image sensors 260(a-n) and two or more lenses for 3D scanning. An example of 3D scanning for surgical navigation using an epipolar geometry configuration includes two image sensors 205(a-n). An example of 3D scanning for surgical navigation using an epipolar geometry configuration includes a projector and an image sensor. P is a point in a 3D space, $p^l$ and $p^r$ are the corresponding object points 250(a-n) on two 2D imaging planes 265(a-n). The focal points of the left lens $o^l$, the focal points of the right lens or and the object point p forms a plane called epipolar plane 210. The intersection between the epipolar plane 210 and left imaging plane 265a is a line called left epipolar line $L^l$ 220a. The intersection between the epipolar plane 210 and the right imaging plane 265n is a line called right epipolar line $L^r$ 220n and $e^l$ is the left epipole 270a and $e^r$ is the right epipole 270n.

The 3D scanning controller 150 may generate the plurality of first epipolar lines 220a positioned in the first image plane 265a of the first 2D intraoperative image 265a. In one aspect, after system calibration, rectification, and un-distortion, each of the first epipolar lines 220a is parallel to each other as positioned in the first image plane 265a. The 3D scanning controller 150 may generate the plurality of second epipolar lines 220n positioned in the second image plane 265n of the second 2D intraoperative image 265n. Each of the second epipolar lines 220n is parallel to each other second epipolar lines 220n as positioned in the second image plane 265n. The 3D scanning controller 150 may convert the first 2D intraoperative image 265a and the second 2D intraoperative image 265n to the 3D intraoperative scan of the patient based on the depth of each object point 250(a-n) provided by each corresponding first epipolar line 220a and second epipolar line 220n as positioned in the corresponding first image plane 265a and second image plane 265n.

The 3D scanning controller 150 may conjugate each first epipolar line 220a positioned in the first imaging plane 265a of the first 2D intraoperative image 260a to each corresponding second epipolar line 220n positioned in the second image plane 265n of the second 2D intraoperative image 260n. The plurality of first epipolar lines 220a and the plurality of second epipolar lines may be a conjugate set. The 3D scanning controller 150 may convert the first 2D intraoperative image 260a and the second 2D intraoperative image 260n to the 3D intraoperative scan of the patient based on the depth of each object point 250(a-n) provided by each corresponding conjugate of each other as positioned in the corresponding first image plane 265a and the second image plane 265n. The search for corresponding image points 265(a-n) between the first 2D intraoperative image 260a and the second 2D intraoperative image 260n is conducted on a first epipolar line 220a and a second epipolar line 220n.

The 3D scanning controller 150 may generate each first epipolar line 220a positioned in the first imaging plane 265a of the first 2D intraoperative image 260a to correspond to a set of first pixels included in the first 2D intraoperative image 260a. The 3D scanning controller 150 may generate each second epipolar line 220n positioned in the second image plane 265n of the second 2D intraoperative image 260 to correspond to a set of second pixels included in the second 2D intraoperative image 260n. The 3D scanning controller 150 may convert the first 2D intraoperative image 260a and the second 2D intraoperative image 260n to the 3D intraoperative scan of the patient based on the depth of each set of first pixels and for each corresponding first epipolar line 220a and the depth of each set of second pixels for each corresponding second epipolar line 220n as positioned in the first image plane 265a and the second image plane 265n.

The 3D scanning controller 150 may generate each first epipolar line 220a positioned in the first image plane 265a of the first 2D intraoperative image 260a to correspond to a row of first pixels included in the first 2D intraoperative image 260a. The 3D scanning controller 150 may generate each second epipolar line 220n positioned in the second image plane 265n to correspond to a row of second pixels included in the second 2D intraoperative image 260n. The 3D scanning controller 150 may convert the first 2D intraoperative image 260a and the second 2D intraoperative image 265n to the 3D intraoperative image scan of the patient based on the depth of each row of first pixels for each corresponding first epipolar line 220a and the depth of each row of second pixels for each corresponding second epipolar line 220n in the first image plane 265a and the second image plane 265n.

The 3D scanning controller 150 may conduct a one-dimensional (1D) search for a corresponding pair of object points 250(a-n) on the first epipolar line 220a of the first image plane 265a of the first 2D intraoperative image 260a and the second epipolar line 220n in the second image plane 265n of the second 2D intraoperative image 265n. The first object point 250(a-n) positioned on the first epipolar line 220a corresponds to a second object point 250(a-n) positioned on the second epipolar line 220n. The 3D scanning controller 150 may convert the 1D search of the corresponding pair of object points 250(a-n) on the first epipolar line 220a and the second epipolar line 220n to the 3D intraoperative scan of the patient based on the depth of the first object point 250(a-n) on the first epipolar line 220a and the corresponding second object point 250(a-n) on the second epipolar line 220n as positioned in the first image plane 265a and the second image plane 265n. In another example, the 3D scanner 160 searches for the corresponding object point pair only on the left epipolar line $L^l$ 220 and the right epipolar line $L^r$ 220n. This one-dimensional search can make the 3D scanning faster than conventional methods that conduct exhaustive search, thereby accelerating surgical navigation. In an embodiment, the 3D scanning controller 150 may conduct a windowed 2D search for a corresponding pair of object points 250(a-n) on the first epipolar line 220a of the first image plane 265a of the first 2D intraoperative image 260a and the second epipolar line 220n in the second image plane 265n of the second 2D intraoperative image 265n.

In another example, the image sensors 205(a-n) used are high speed complementary metal-oxide-semiconductor (CMOS) image sensors. This make the 3D scanning process very fast. For instance, the frame rate of 3D scanning may be beyond 100 frame per second, up to 4000 frame per second. In another example, the 3D scanner 160 includes two or more image sensors 205(a-n), two or more lenses, and a pattern generator 165. The pattern generator 165 may generate patterns to be projected on the patients to be scanned. It is advantageous to create patterns via light on the patient to be imaged by the image sensors 205(a-n). The patterns can help improve the robustness and accuracy of the 3D scan and therefore improve surgical navigation.

In one example, the pattern generator 165 includes one or more light emitting diodes (LEDs) and a patterned aperture. The patterned aperture may be made of metals, ceramics or plastics. The patterned apertures with the LEDs created patterns that may be combined with the information of the patient anatomy, which increases the accuracy and speed of the 3D scanning. The patterned aperture and epipolar geometry combined can facilitate more accurate scanning of patient anatomy. Improved 3D scan can enhance the image registration between intraoperative 3D scan and preoperative images (e.g. MRI and CT), thereby improving the surgical navigation. It should be appreciated that other illumination devices such as a halogen lamp, a xenon lamp, an arc lamp, a laser diode may be used instead of an LED.

In another example, the 3D scanner 160 includes or more image sensors 205(a-n), two or more lenses, and a pattern generator 165 that includes one or more LEDs and a digital micromirror device. The LED and digital micromirror device may be controlled by the 3D scanning controller 150 to create patterns desirable for the 3D scanning application in medicine. The digital micromirror device with the LEDs created patterns that may be projected on the patient anatomy, which increases the accuracy and speed of the 3D scanning. The digital micromirror device and epipolar geometry combined can facilitate more accurate scanning of patient anatomy. Improved 3D scan can enhance the image registration between intraoperative 3D scan and preoperative images (e.g. MRI and CT), thereby improving the surgical navigation. It should be appreciated that other illumination devices such as a halogen lamp, a xenon lamp, an arc lamp, a laser diode may be used instead of an LED. In one example, the patterns created Is dynamic where the pattern changes temporarily, so that any residual pattern-to-depth dependence may be reduced.

In yet another example, the 3D scanner 160 includes two or more image sensors 205(a-n), two or more lenses, and a pattern generator 165 that includes one or more LEDs and a thin-film-transistor liquid-crystal display. The LED and thin-film-transistor liquid-crystal display 120 may be controlled by the 3D scanning controller 150 to generate patterns desirable for the 3D scanning application in medicine. The thin-film-transistor liquid-crystal display 120 with the LEDs generated patterns that may be projected on the patient anatomy, which increases the accuracy and speed of the 3D scanning. The thin-film-transistor liquid-crystal display 120 and epipolar geometry combined may facilitate more accurate scanning of patient anatomy. Improved 3D scan may enhance the image registration between intraoperative 3D scan and preoperative images (e.g. MRI and CT), thereby improving the surgical navigation. It should be appreciated that other illumination devices such as a halogen lamp, a xenon lamp, an arc lamp, a laser diode may be used instead of an LED. In one example, the patterns created may be dynamic where the pattern changes temporarily, so that any residual pattern-to-depth dependence may be reduced.

In yet another example, the 3D scanner 160 includes two or more image sensors 205(a-n), two or more lenses, and a pattern generator 165 that includes one or more edge emitting laser, at least one collimating lens, and at least one diffractive optics element. The edge emitting laser and the diffractive optics element may be controlled by the 3D scanning controller 150 to create patterns desirable for the 3D scanning application in medicine. An example of a pattern creator comprises an edge emitting laser, a collimating lens, and a diffractive optics element. The edge emitting laser, the collimating lens and the diffractive optics element created patterns that may be projected on the patient anatomy, which increases the accuracy and speed of the 3D scanning. The edge emitting laser, the diffractive optics element and epipolar geometry combined may facilitate more accurate scanning of patient anatomy. An improved 3D scan may enhance the image registration between intraoperative 3D scan and preoperative images (e.g. MRI and CT), thereby improving the surgical navigation. It should be appreciated that other illumination devices such as LEDs, a halogen lamp, a xenon lamp, an arc lamp, a laser diode may be used instead of an edge emitting laser. In one example, the patterns created Is dynamic where the pattern changes temporarily, so that any residual pattern-to-depth dependence may be reduced.

In another example, the 3D scanner comprises 2 or more image sensors, 2 or more lenses, and a pattern creator that comprises at least one patterned vertical cavity semiconductor emission laser array, at least one collimating lens, and at least one diffractive optics element. The patterned vertical cavity semiconductor emission laser array and the diffractive optics element may be controlled by the 3D scanning controller to create patterns desirable for the 3D scanning application in medicine. An example of a pattern creator comprises a patterned vertical cavity semiconductor emission laser array, a collimating lens, and a diffractive optics element. The patterned vertical cavity semiconductor emission laser array, the collimating lens and the diffractive optics element creates patterns that may be projected on the patient anatomy, which increases the accuracy and speed of the 3D scanning. The patterned vertical cavity semiconductor emission laser array, the diffractive optics element and epipolar geometry combined can facilitate more accurate scanning of patient anatomy. Improved 3D scan can enhance the image registration between intraoperative 3D scan and preoperative images (e.g. MRI and CT), thereby improving the surgical navigation. In one example, the patterns created Is dynamic where the pattern changes temporarily, so that any residual pattern-to-depth dependence may be reduced.

In another embodiment, the 3D scanner includes two or more infrared-sensitive image sensors 205(a-n), two or more infrared-compatible lenses, and an infrared pattern generator 165. The 3D scanner 160 may further include two or more infrared optical filters. In one example, the infrared optical filters are used in conjunction with infrared-sensitive image sensors 205(a-n) and infrared-compatible lenses to capture infrared images 260(a-n). In one example, the infrared range are beyond 800 nm. The infrared optical filters may be bandpass filters or long-pass filters (e.g. 800 nm long pass filters or 830 nm band pass filters). In one aspect, the infrared-sensitive image sensors 205(a-n) may be high speed infrared-sensitive CMOS image sensors 205(a-n). In one example, the infrared pattern generator 165 includes one or more light emitting diodes (LEDs) and a patterned aperture. In another example, the infrared pattern generator 165 includes one or more infrared LEDs and an infrared-compatible digital micromirror device. In yet another example, the infrared pattern generator 165 includes one or more LEDs and an infrared-compatible thin-film-transistor liquid-crystal display 120. In yet another example, the infrared pattern generator 165 includes one or more infrared edge emitting laser, at least one infrared-compatible collimating lens, and at least one diffractive optics element. In yet another example, the infrared pattern generator includes at least one infrared patterned vertical cavity semiconductor emission laser array, at least one infrared-compatible collimating lens, and at least one diffractive optics element. It should be appreciated that other infrared illumination devices such as an infrared halogen lamp, an infrared xenon lamp, an infrared arc lamp, an infrared laser diode may be used. In one example, the infrared patterns created are dynamic where the infrared pattern changes temporarily, so that any residual pattern-to-depth dependence may be reduced.

3D Scanner with Statistical Pattern Generator

Figure 3:
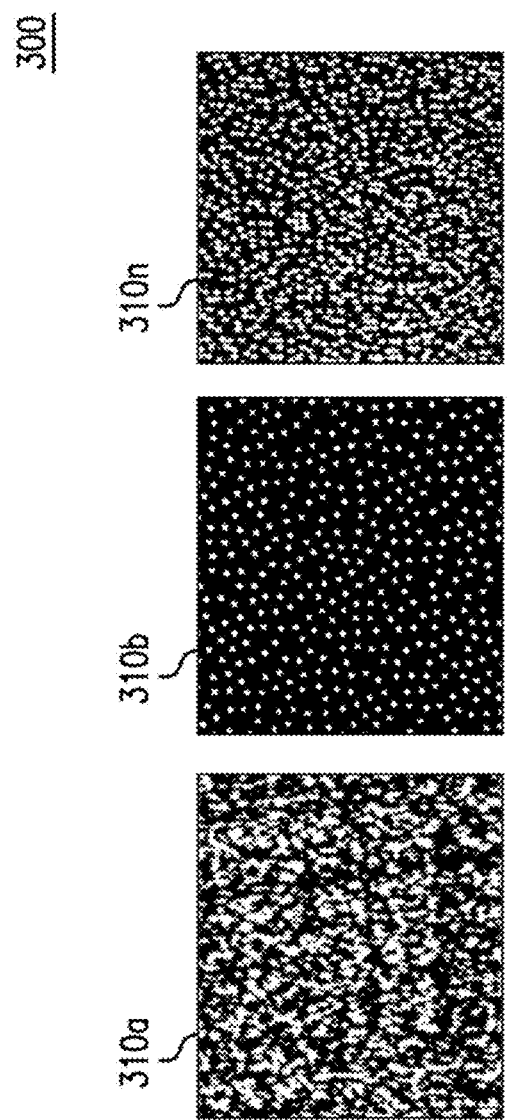
FIG. 3 is a schematic view of random patterns that the statistical pattern generator may generate.

In another embodiment, the 3D scanner 160 includes at least one image sensor 205(a-n), at least one lens, and a statistical pattern generator 165. The statistical pattern generator may generator random patterns and/or pseudo-random patterns. The random patterns and/or pseudo-random patterns may be projected to the patient to facilitate the 3D scanning of patient anatomy. The improved 3D scan may enhance the image registration between intraoperative 3D scan and preoperative images (e.g. MRI and CT), thereby improving the surgical navigation. Examples of random patterns and/or pseudo-random patterns that the statistical pattern generator 165 may generate may be shown in a statistical pattern configuration 300 shown in FIG. 3. For instance, the random patterns 310(a-n), where n is an integer equal to or greater than one, may be very dense: for example, between 20,000 and 300,000 random dots may be used. Different from previous embodiments, only one image sensor 205(a-n) is needed for this embodiment using a statistical pattern generator 165.

The surgical imaging and navigation system 100 may include a 3D scanner 160 that includes a projector, an image sensor 205n, and a pattern generator 165. The pattern generator 165 may generate a pseudo random pattern 310(a-n) that includes a plurality of dots. Each position of each corresponding dot included in the pseudo random pattern 310(a-n) may be pre-determined by the pattern generator 165. The projector may project the pseudo random pattern 310(a-n) onto the patient. Each position of each corresponding dot included in the pseudo random pattern 310(a-n) is projected onto a corresponding position on the patient. The image sensor 205n may capture a 2D intraoperative image of a plurality of object points 250(a-n) associated with the patient.

The 3D scanning controller 150 may associate each object point 250(a-n) associated the patient that is captured by the image sensor 205n with a corresponding dot included in the pseudo random pattern 310(a-n) that is projected onto the patient by the projector based on the position of each corresponding dot as pre-determined by the pattern generator 165. The 3D scanning controller 150 may convert the 2D intraoperative image 260n to the 3D intraoperative scan of the patient based on the association of each object point 250(a-n) to each position of each corresponding dot included in the pseudo random pattern as pre-determined by the pattern generator 165.

The controller 110 may co-register pre-operative image data captured from at least one pre-operative image of the patient with intraoperative image data provided by the 3D intraoperative image scan. The controller 110 may instruct a display 120 to display the co-registered pre-operative image data as captured from at least one pre-operative image with the intraoperative image data provided by the 3D intraoperative scan as the surgeon navigates during the surgical navigation.

The projector may project the pseudo random pattern 310(a-n) onto a 2D surface before the patient is positioned on the 2D surface. The image sensor 205n may capture a 2D image of the pseudo random pattern onto the 2D surface before the patient is positioned on the 2D surface. The 3D scanning controller 150 may calibrate each position of each dot included in the pseudo random pattern 310(a-n) as projected onto the 2D surface and pre-determined by the pattern generator 165 to each corresponding position of each dot as included in the 2D image 260n captured by the image sensor 205n. The 3D scanning controller 150 may compare each positon of each dot included in the pseudo random pattern 310(a-n) as projected onto the 2D surface and pre-determined by the pattern generator 165 to each position of each dot included in the pseudo random pattern 310(a-n) as projected onto the patient. The 3D scanning controller 150 may determine each depth of each object point 250(a-n) as captured in the 2D intraoperative image 260n by the image sensor 205n of the patient when the projector projects the pseudo random pattern 310(a-n) onto the patient after the calibration based on a difference in depth of each corresponding dot included in the pseudo random pattern 310(a-n) as projected onto the 2D surface as compared to each corresponding dot included in the pseudo random pattern 310(a-n) as projected onto the patient. The 3D scanning controller 150 may convert the 2D intraoperative image 205n to the 3D intraoperative scan of the patient based on the depth of each object point 250(a-n) as provided by the calibration of the pseudo random pattern 310(a-n) to the 2D intraoperative image 260n.

The 3D scanning controller 150 may determine a plurality of first epipolar lines 220a associated with a projection image plane 265a of the projection of the pseudo random pattern 310(a-n) and a plurality of second epipolar lines 220n associated with the 2D intraoperative image plane 265n of the captured 2D intraoperative image 260n based on an epipolar plane 210 that triangulates the plurality of object points 250(a-n) included in the 2D intraoperative image 260n to the plurality of dots 250(a-n) included in the pseudo random pattern 310(a-n). Each epipolar line 220(a-n) provides a depth of each object point 250(a-n) as projected from the projection image plane 265a associated with the projector and the 2D intraoperative image plane 265n associated with the 2D intraoperative image 260n. The 3D scanning controller 150 may convert the 2D intraoperative image 260n to the 3D intraoperative image scan of the patient based on the depth of each object point 250(a-n) provided by each corresponding epipolar line 220(a-n).

In one example, the statistical pattern generator 165 may include one or more edge emitting laser, at least one collimating lens, and at least one diffractive optics element. The edge emitting laser and the diffractive optics element may be controlled by the 3D scanning controller 150 to generate patterns 310(a-n) desirable for the 3D scanning application in medicine. The edge emitting laser and the diffractive optics element generated patterns 310(a-n) that may be projected on the patient anatomy, which increases the accuracy and speed of the 3D scanning. Improved 3D scan may enhance the image registration between the intraoperative 3D scan and preoperative images (e.g. MRI and CT), thereby improving the surgical navigation. It should be appreciated that other illumination devices such as LEDs, a halogen lamp, a xenon lamp, an arc lamp, a laser diode may be used instead of an edge emitting laser. In one example, the pattern 310(a-n) generated is dynamic where the pattern changes temporarily, so that any residual pattern-to-depth dependence may be reduced.

In another example, the statistical pattern generator 165 includes at least one patterned vertical cavity semiconductor emission laser array, at least one collimating lens, and at least one diffractive optics element. The patterned vertical cavity semiconductor emission laser array and the diffractive optics element may be controlled by the 3D scanning controller 150 to create patterns desirable for the 3D scanning application in medicine. The patterned vertical cavity semiconductor emission laser array and the diffractive optics element generates patterns 310(a-n) that may be projected on the patient anatomy, which increases the accuracy and speed of the 3D scanning. The improved 3D scan may enhance the image registration between intraoperative 3D scan and preoperative images (e.g. MRI and CT), thereby improving the surgical navigation. In one example, the patterns 310(a-n) generated are dynamic where the pattern changes temporarily, so that any residual pattern-to-depth dependence may be reduced.

In another example, the statistical pattern generator 165 includes one or more laser diodes and a statistically patterned aperture. The statistically patterned aperture may be made of metals, ceramics or plastics. In one aspect, the statistically patterned apertures with the laser diodes created patterns 310(a-n) that may be combined with the information of the patient anatomy, which increases the accuracy and speed of the 3D scanning. Improved 3D scan may enhance the image registration between intraoperative 3D scan and preoperative images (e.g. MRI and CT), thereby improving the surgical navigation. It should be appreciated that other illumination devices such as halogen lamp, xenon lamp, arc lamp, LED may be used instead of a laser diode.

In another embodiment, the 3D scanner 160 includes one infrared-sensitive image sensor 205n, an infrared-compatible lens, an optical filter, and an infrared statistical pattern generator 165. In one example, the optical filter is used in conjunction with the infrared-sensitive image sensor 205n and infrared-compatible lens to capture infrared images (e.g. optical filter passes through at least part of the infrared spectrum). In one example, the infrared range is beyond 800 nm. The optical filter may be a bandpass filter or a long-pass filter (e.g. 800 nm long pass filters or 830 nm band pass filters). The infrared-sensitive image sensor 205n may be a high-speed infrared-sensitive CMOS image sensor. In one example, the infrared pattern generator 165 includes one or more laser diode and a statistically patterned aperture. In another example, the infrared statistical pattern generator 165 includes one or more infrared edge emitting laser, at least one infrared-compatible collimating lens, and at least one diffractive optics element. In yet another example, the infrared statistical pattern generator 165 includes at least one infrared patterned vertical cavity semiconductor emission laser array, at least one infrared-compatible collimating lens, and at least one diffractive optics element. It should be appreciated that other infrared illumination devices such as an infrared halogen lamp, an infrared xenon lamp, an infrared arc lamp, an infrared laser diode may be used. In one example, the infrared pattern 310(a-n) generated may be dynamic where the infrared pattern 310(a-n) changes temporarily, so that any residual pattern-to-depth dependence may be reduced.

3D Scanner with Non-Statistical Projection Pattern Generator

In another embodiment, the 3D scanner 160 includes at least one image sensor 205(a-n), at least one imaging lens, and a non-statistical projection pattern generator 165. The non-statistical projection pattern generator 165 may create dynamic patterns 410(a-n), where n is an integer equal to or greater than one, that are non-statistical. In an example, the non-statistical projection pattern generator 165 may generate dynamic patterns 410(a-n) with spatial coding in spatial domain, frequency domain, or a combination thereof. The patterns 410(a-n) may be projected to the patient to facilitate the 3D scanning of patient anatomy. The patterns 410(a-n) may be projected dynamically: a series of patterns 410(a-n) are projected to properly encode the spatial information to facilitate 3D scanning, greatly reducing pattern-to-depth dependence. Improved 3D scan may enhance the image registration between intraoperative 3D scan and preoperative images (e.g. MRI and CT), thereby improving the surgical navigation.

The surgical imaging and navigation system 100 may include a 3D scanner 160 that includes a projector, an image sensor 205n, and a pattern generator 165. The pattern generator 165 may generate a plurality of non-statistical patterns 410(a-n) with each non-statistical pattern 410(a-n) including a plurality of identified characteristics. Each plurality of identified characteristics associated with each non-statistical pattern 410(a-n) may have different variations of each other. The projector may project each non-statistical pattern 410(a-n) onto the patient in series. Each variation in the identified characteristics of each non-statistical pattern 410(a-n_ as projected onto the patient is adjusted based on when in the series each corresponding non-statistical pattern 410(a-n) is projected onto the patient. The image sensor 205n may capture a 2D intraoperative image 260n of a plurality of object points 250(a-n) with the patient after each non-statistical pattern 410(a-n) is projected onto the patient.

The 3D scanning controller 150 may identify a position of each object point 250(a-n) associated with the patient that is captured by the image sensor 205n after each non-statistical pattern 410(a-n) is projected onto the patient. The 3D scanning controller 150 may determine an actual position of each object point 250(a-n) after the plurality of non-statistical patterns 410(a-n) is projected onto the patient based on an average position of each object point 250(a-n) determined from each identified position of each object point 250(a-n) as generated after each non-statistical pattern 410(a-n) is projected onto the patient. The 3D scanning controller 150 may convert the 2D intraoperative image 260n to the 3D intraoperative scan of the patient based on the actual position of each object point 250(a-n) after the plurality of non-statistical patterns is projected onto the patient.

The controller 110 may co-register pre-operative image data captured from at least one pre-operative image of the patient with intraoperative image data provided by the 3D intraoperative image scan. The controller 110 may instruct the display 120 to display the co-registered pre-operative image data as captured from the at least one pre-operative image with the intraoperative image data provided by the 3D intraoperative scan as the surgeon navigates during the surgical operation.

The pattern generator 165 may generate the plurality of non-statistical patterns 410(a-n) with each non-statistical pattern 410(a-n) being a variation in scale from each other non-statistical pattern 410(a-n) that is projected onto the patient. The pattern generator 165 may generate a first non-statistical pattern that includes a strip with a resolution that is decreased to a resolution that the projector is capable to project and the image sensor 205n is capable to capture. The pattern generator 165 may generate each additional non-statistical pattern 410(a-n) that includes a stripe being an increased variation in scale from the first non-statistical pattern 410(a-n) and each additional non-statistical pattern 410(a-n) is a variation from each other additional non-statistical pattern 410(a-n) in the resolution of each stripe associated with each additional non-statistical pattern 410(a-n).

The projector may project each non-statistical pattern 410(a-n) that varies in resolution to each corresponding horizontal row of pixels included in the 2D intraoperative image 260n captured by the image sensor 205n. The projector may project each non-statistical pattern 410(a-n) that varies in resolution to each corresponding vertical column of pixels included in the 2D intraoperative image 260n captured by the image sensor 205n. The 3D scanning controller 150 may determine each depth of each object point 250(a-n) as captured in the 2D intraoperative image 260n by the image sensor 205n of the patient based on a depth associated with each pixel included in the 2D intraoperative image 260n that is determined after each non-statistical pattern 410(a-n) is projected onto the patient. The 3D scanning controller 150 may convert the 2D intraoperative image 260n to the 3D intraoperative scan of the patient based on the depth of each object point 250(a-n) as determined after the plurality of statistical patterns 410(a-n) is projected onto the patient.

The 3D scanning controller 150 may determine a plurality of first eipolar lines 220a with a projection image plane 265a of the projection of the plurality of non-statistical patterns 410(a-n) and a plurality of second epipolar lines 220n associated with a 2D intraoperative image plane 265n of the captured 2D intraoperative image 260n based on an epipolar plane 210 that triangulates the plurality of object points 250(a-n) generated when each non-statistical pattern 410(a-n) is applied to the 2D intraoperative image 260n to the plurality of object points 250(a-n) included in the 2D intraoperative image 260n. Each epipolar line 220(a-n) provides a depth of each object point 250(a-n) as projected from the projection image plane 265a associated with the projector and the 2D intraoperative image plane 265n associated with the 2D intraoperative image 260n. The 3D scanning controller 150 may convert the 2D intraoperative image 260n to the 3D intraoperative scan of the patient based on the depth of each object point 250(a-n) provided by each corresponding epipolar line 220(a-n).

In one embodiment, the non-statistical projection pattern generator 165 includes one or more LEDs, at least one lens, and a digital micromirror device. The LED and the digital micromirror device may be controlled by the 3D scanning controller 150 to generate patterns 410(a-n) desirable for the 3D scanning application in medicine. In another embodiment, the non-statistical projection pattern generator 165 includes one or more LEDs, at least one lens, and a thin-film-transistor liquid-crystal display 120. The LED and thin-film-transistor liquid-crystal display 120 may be controlled by the 3D scanning controller 150 to generate patterns 165 desirable for the 3D scanning application in medicine. It should be appreciated that other illumination devices such as a halogen lamp, a xenon lamp, an arc lamp, a laser diode may be used instead of an LED.

In yet another embodiment, the 3D scanner 160 includes at least one infrared-sensitive image sensor 205n, at last one infrared-compatible imaging lens, at least one optical filter, and an infrared non-statistical projection pattern generator 165. In one example, the optical filter is used in conjunction with the infrared-sensitive image sensor 205a and the infrared-compatible lens to capture infrared images 205n. In one example, the infrared range are beyond 800 nm. The optical filter may be a bandpass filter or a long-pass filter (e.g. 800 nm long pass filters or 830 nm band pass filters). The infrared-sensitive image sensor 205n may be a high-speed infrared-sensitive CMOS image sensor. In one example, the infrared non-statistical projection pattern generator 165 includes one or more infrared LEDs, at least one infrared-compatible lens, and a digital micromirror device. The infrared LED and the digital micromirror device may be controlled by the 3D scanning controller 150 to generate dynamic infrared patterns 410(a-n) desirable for the 3D scanning application in medicine. In another embodiment, the infrared non-statistical projection pattern 165 includes one or more infrared LEDs, at least one infrared-compatible lens, and a thin-film-transistor liquid-crystal display 120. The infrared LED and thin-film-transistor liquid-crystal display 120 may be controlled by the 3D scanning controller 150 to create dynamic infrared patterns 410(a-n) desirable for the 3D scanning application in medicine. It should be appreciated that other infrared illumination devices such as an infrared halogen lamp, an infrared xenon lamp, an infrared arc lamp, an infrared laser diode may be used instead of an infrared LED.

Figure 4:
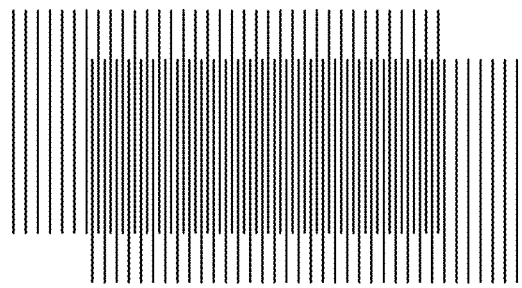
FIG. 4 illustrates a schematic view of dynamic patterns that the non-statistical pattern generator generates such as binary code, stripe boundary code, and miere pattern.
Figure 4:
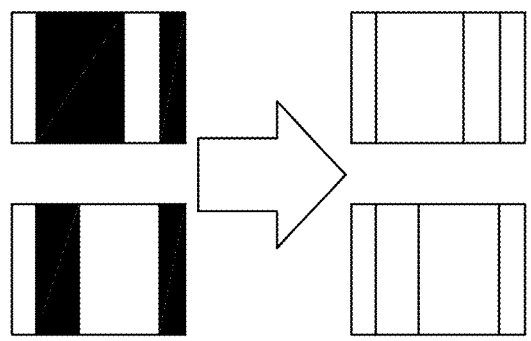
Figure 4:
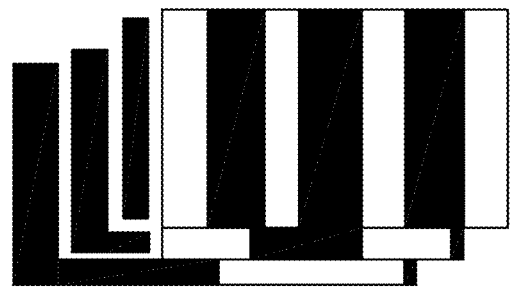

With the aforementioned apparatuses and systems, the dynamic projection pattern 410(a-n) may be created to facilitate 3D scanning. A few examples of dynamic patterns 410(a-n) that the non-statistical projection pattern generator 165 creates are shown in non-statistical pattern configuration 400 in FIG. 4 such as binary code, stripe boundary code, and miere pattern. In one embodiment, binary codeword 410a is represented by a series of black and white stripes. If black represents 1 and white represents 0, the series of 0 and 1 at any given location may be encoded by the dynamic projection pattern 410a (varies temporarily); the binary dynamic projection pattern 410a may be captured by the image sensor 205n and lens, and decoded to recover the binary codeword that encodes an location (e.g. 10100011). In theory, N binary patterns 410a may generate 2N different codewords per image dimension (x or y dimension). A representative binary pattern 410 is illustrated in FIG. 4. Similarly, binary coding may be extended to N-bits coding. For example, instead of binary case where only 1 and 0 are represented by black and white, a N-bits integer may be represented by an intensity in between. For instance, if it is a 2-bit encoding system, $2^2=4$ different possibilities. If maximum intensity is I, 0, 1, 2, 3 may be represented by I, $\frac{2}{3}*I$, $\frac{1}{3}*I$, and 0, respectively. In other examples, dynamic stripe boundary code-based projection or the dynamic Moire code-based projection may be implemented.

In another embodiment, dynamic Fourier transform profilometry may be implemented by the aforementioned apparatuses and systems. In one aspect, periodical signals are generated to carry the frequency domain information including spatial frequency and phase. Inverse Fourier transform of only the fundamental frequency results in a principle phase value ranging from $-\pi$ to $\pi$. After spatial or temporal phase unwrapping (The process to remove $2\pi$ discontinuities and generate continuous map), actual 3D shape of patient anatomy may be recovered. Fourier transform profilometry is less sensitive to the effect of out-of-focus images of patients, making it a suitable technology for intraoperative 3D scanning. Similarly, $\pi$-shifted modified Fourier transform profilometry may be implemented intraoperatively, where a $\pi$-shifted pattern is added to enable the 3D scanning.

In another example, a DC image may be used with Fourier transform profilometry. By capturing the DC component, the DC-modified Fourier transform profilometry may improve 3D scan quality intraoperatively. In another example, N-step phase-shifting Fourier transform profilometry may be implemented intraoperatively. It should be appreciated that the larger the number of steps (N) is chosen, the higher the 3D scanning accuracy. For instance, three-step phase-shifting Fourier transform profilometry may be implemented to enable high speed 3D scanning intraoperatively. It should be appreciated that periodical patterns such as trapezoidal, sinusoidal, or triangular pattern may be used in the Fourier transform profilometry for intraoperative 3D scan. It should be further appreciated that windowed Fourier transform profilometry, two-dimensional Fourier transform profilometry, or wavelet Fourier transform profilometry may also be implemented by the aforementioned apparatuses and systems. It should be appreciated more than one frequency of periodical signal (e.g. dual frequencies) may be used in the modified Fourier transform profilometry, so that phase unwrapping become optional in the intraoperative 3D scan. The dynamic Fourier transform profilometry and modified Fourier transform profilometry discussed herein may improve the quality of 3D scan of the patient. Improved 3D scan may enhance the image registration between intraoperative 3D scan and preoperative images (e.g. MRI and CT), thereby improving the surgical navigation.

In yet another embodiment, the aforementioned apparatuses and systems implement Fourier transform profilometry or modified Fourier transform profilometry, in combination with binary codeword projection. The Fourier transform profilometry and binary codeword projection may be implemented sequentially, concurrently, or a combination thereof. The combined approach may improve the 3D scanning accuracy, albert at the cost of 3D scanning speed. Improved 3D scan may enhance the image registration between intraoperative 3D scan and preoperative images (e.g. MRI and CT), thereby improving the surgical navigation.

Figure 5:
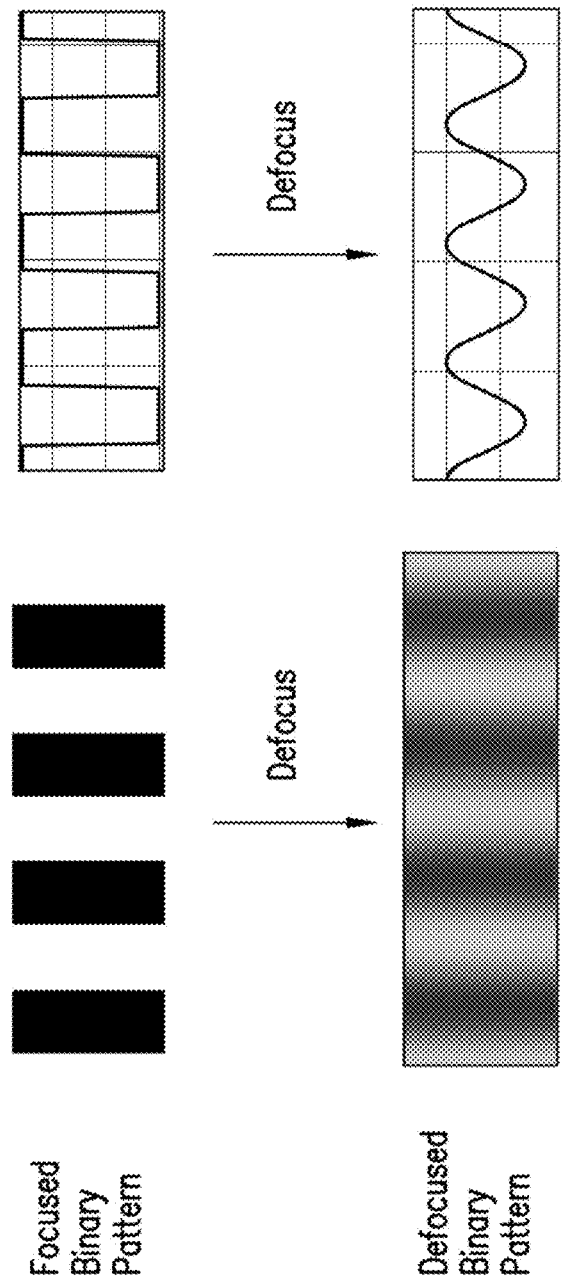
FIG. 5 illustrates a schematic view of defocusing a binary pattern in the defocusing configuration.

In another embodiment, the aforementioned non-statistical projection pattern generator may include at least one lens. The lens is configured such a way so that the projected pattern(s) are defocused. The process of defocusing a binary pattern is illustrated in the defocusing configuration 500 depicted in FIG. 5. The defocusing process by the lens is similar a convolution of gaussian filter on the binary pattern. Consequently, the defocused binary pattern may create periodical patterns that are similar to sinusoidal patterns.

In another example, dithering techniques are used to generated high-quality periodical fringe patterns through binarizing a higher order bits fringe pattern (e.g. 8 bits) such as sinusoidal fringe patterns. In one example, ordered dithering is implemented; for example, Bayer matrix may be used to enable ordered dithering. In another example, error-diffusion dithering is implemented; for instance, Floyd-Steinberg (FS) dithering or minimized average error dithering may be implemented. It should be appreciated that in some cases the dithering techniques may be implemented in combination with defocusing technique to improve the quality of intraoperative 3D scan.

The 3D scanning controller 150 controls the modes and properties of 3D scanner 160. For instance, the size of the area of 3D scanning, the resolution of 3D scanning, the speed of 3D scanning, the timing of 3D scanning may be controlled by the 3D scanning controller 150. The 3D scanning controller 150 may also implement the aforementioned methods of 3D scanning. It should also be appreciated that the 3D scanning controller 150 may include the necessary hardware, software, or combination thereof to carry out the 3D scanning methods previously discussed. The 3D scanning controller 150 may include a microcontroller, a Field Programmable Gate Array (FPGA), a mobile or desktop computer that may include a graphics processing unit (GPU), an application-specific integrated circuit (ASIC), or a combination thereof.

Imaging Detector and Imaging Controller

The imaging detector 180 can capture the images intraoperatively. In one embodiment, the imaging detector 180 is a color image sensor with a lens. In one aspect, the color camera uses a Bayer filter pattern at the pixel level to detect color components of red, green and blue. In another example, the imaging detector 180 is a monochrome camera that can detect near infrared signal. It should be appreciated that in some cases the 3D scanner 160 already enable intraoperative imaging; therefore, no additional imaging detector is needed. In one example, the 3D scanner 160 comprises at least one color image sensor and a lens, and the color image camera and the lens can also serve as the imaging detector 180 to capture intraoperative color image. Therefore, the imaging detector 180 and the 3D scanner 160 share hardware including said color image sensor and said lens. In another example, the 3D scanner 160 comprises at least one infrared-sensitive image sensor and an infrared-compatible lens, and the infrared-sensitive image sensor and an infrared-compatible lens can also serve as the imaging detector 180 to capture intraoperative infrared image. Therefore, the imaging detector 180 and the 3D scanner 160 share hardware including said infrared-sensitive image sensor and said infrared-compatible lens.

In another embodiment, the imaging detector 180 enable special purpose imaging, such as fluorescence imaging, hyperspectral imaging, thermal imaging, polarization imaging, photoacoustic imaging, etc. In one example, the imaging detector comprises a monochrome camera and a fluorescence emission filter. For instance, the fluorescence filter may be an 830 nm band pass filter to enable imaging of indocyanine green.

In another embodiment, the imaging detector 180 enable other intraoperative imaging modalities. In one example, the imaging detector 180 is an ultrasound transducer; therefore, intraoperative ultrasound may be enabled. In another example, the imaging detector 180 is a fluoroscope; therefore, fluoroscopy may be enabled (2D or 3D fluoroscopy). In yet another example, the imaging detector 180 is a C-arm X-ray scanner. In yet another example, the imaging detector 180 is an x-ray computed tomography scanner (CT); therefore, intraoperative CT may be enabled. In yet another example, the imaging detector is a Magnetic resonance imaging (MRI) scanner; therefore, intraoperative MRI may be enabled; in yet another example, the imaging detector 180 is a optical coherence tomography (OCT) scanner; therefore, intraoperative OCT scanning may be enabled.

The imaging controller 170 can control the acquisition, storage, and processing of the images captured by the imaging detector 180. In one aspect, the frame rate, field of view, magnification, and gain level of imaging detector 180 may be controlled. In another aspect, the imaging controller 170 can synchronize the image acquisition with the modulation and frequency of the illumination to enable synchronized imaging capturing under modulated illumination. In another example, the imaging controller 170 controls the acquisition and reconstruction of intraoperative CT scan. In yet another example, the imaging controller 170 controls the acquisition and reconstruction of intraoperative MRI scan. When there is more than one mode of imaging, the imaging controller 170 can also select and mode of image acquisition.

It should be appreciated that the imaging detector may share common hardware with other components of the systems. In one example, the 3D scanner 160 already enable color imaging; therefore, no standalone imaging detector is needed. In another example, the tracker 130 already enable infrared imaging; therefore, no standalone imaging detector is needed.

It should also be appreciated that the imaging controller 170 may include the necessary hardware, software, or a combination thereof to carry out the imaging functions previously discussed. The imaging controller 170 may comprise a microcontroller, a Field Programmable Gate Array (FPGA), a mobile or desktop computer that may include a graphics processing unit (GPU), an application-specific integrated circuit (ASIC), or a combination thereof.

Light Source and Light Source Controller

The light source 195 can provide general-purpose and/or special-purpose illumination for surgical guidance. In one embodiment, the light source 195 is a plurality of light emitting diodes (LEDs). The LEDs may be arranged in such a way to minimize the shadows produced by individual LEDs. A plurality of individual LEDs may be spaced apart to project light onto the patient, so that shadow cast by an intervening object is negated by at least one other of a plurality of individual LEDs.

It should also be appreciated that the light source 195 may be based on other technologies, such as incandescent light lamp, laser diode, arc-lamp, laser, as well as coherent or in-coherent light sources. It should also be appreciated that the light source 195 may also include one or a plurality of light diffusers to homogenize the illumination. It should also be appreciated that the light source 195 may also include one or a plurality of collimation lenses to collimate the illumination.

In another embodiment, the light source 195 provides fluorescence excitation for fluorescence imaging, in conjunction with the aforementioned imaging detector 180. The light source 195 may comprise one or a plurality of spectral filters. In one aspect, one or more 775 nm low pass filters may be used with white and near infrared LEDs to enable fluorescence excitation with indocyanine green.

In some embodiments, the light source controller 190 may control the light source 195 to provide pulsed and/or modulated illumination. Frequency modulation, pulse-duration modulation, amplitude modulation, or phase modulation may be implemented. In one aspect, the illumination is modulated at a frequency so that the illumination does not interfere with the 3D scanning performed by the 3D scanner 160. In another aspect, the illumination is modulated to be a DC signal so that the illumination does not interfere with the 3D scanning performed by the 3D scanner 160. In yet another aspect, the illumination is modulated at a frequency so that the illumination may be detected by the imaging detector 180 and imaging controller 170.

The light source controller 190 can control the intensity, mode, frequency, modulation of the light source 195. In one aspect, the light source controller 190 can synchronize the image acquisition with the modulation and frequency of the illumination to enable synchronized imaging capturing under modulated illumination. When there is more than one mode of illumination, the imaging controller 170 can also select the mode of illumination provided by the light source 195. In another aspect, the light source 195 is synchronized with the 3D scanner 160 to enable 3D scanning and illumination in a sequentially interleaved fashion. In another aspect, the light source 195 is synchronized with the tracker 130 to enable 3D scanning and tracking in a sequentially interleaved fashion.

It should be appreciated that the light source 195 may share common hardware with other components of the systems. In one example, the 3D scanner 160 already enable surgical illumination; therefore, no standalone light source is needed. In another example, the imaging detector 180 already enable fluorescence excitation; therefore, no standalone light source is needed.

Image Registration Process

The image registration between intraoperative 3D scan and other image data (e.g. preoperative/intraoperative CT or MRI) build correspondences between patient anatomy and medical imageries. This can provide surgical guidance and help surgical decision making of the surgeon.

The image registration is performed by the controller 110. In some embodiments, the controller 110 comprises a graphics processing unit (GPU) that can accelerate the image registration process. Pre-operative or intraoperative image data such as CT (x-ray computerized tomography) or magnetic resonance imaging (MRI) may be registered to the 3D scan and/or surgical imaging provided by the system 100. The 3D image data captured by the system 100 may be in the form of point clouds, or polygon mesh, or other formats that can represent 3D shape.

The user may define the regions of interest. For instance, L2 and L3 of lumber spine may be defined as the region of interest for image registration. The algorithm may automatically segment out certain organs or tissues to facilitate image registration (e.g. automatic segmentation and labelling of vertebrae based on the CT image). The definition of region-of-interest can expedite the registration process. Once the two datasets (e.g. CT and intraoperative 3D scan) are registered, the full data set may be displayed (e.g. full lumber spine based on preoperative CT data, instead of region of interest containing only L2 and L3).

In one embodiment, a surface-based image registration algorithm is implemented for image registration. For surface-based image registration, the surface(s) of the intraoperative data and preoperative data are matched. In one example, iterative closest point (ICP) method is used for surface registration. For instance, the algorithm can minimize the difference between a first point cloud (representing intraoperative 3D data captured by the system 100) and a second point cloud (representing preoperative 3D point cloud captured by the CT or MRI). In another example, a modified K-D tree algorithm may be implemented with ICP for efficient closest point computation to enable subset-subset matching. It should be appreciated that the ICP method may be implemented with parallelization using GPU.

The 3D scanner 160 may acquire an intraoperative 3D scan of a surgical field. The medical image data (e.g., CT or MRI) may be loaded. The controller 110 may perform segmentation on the medical image data (e.g., CT or MRI) to isolate the organ of interest (e.g., 1.5 of lumber spine for spine surgery). The controller 110 may reduce the image data into surface data of the organ of interest (e.g., surface of L5 of lumber spine). The controller 110 may perform surface-based image registration between the surface data of the organ of interest and the intraoperative 3D scan.

It should be appreciated that in some embodiments only a subset of the surface data of organ of interest is used. In one example, only the posterior portion of the surface data of vertebral body Lumber 5 (L5) is used for surface registration. It should also be appreciated that in some embodiments only a subset of the intraoperative 3D scan data is used. In one example, only the intraoperative 3D scan data near the surgical field is used for surface registration.

The 3D scanner may acquire an intraoperative 3D scan of the surgical field. The controller 110 may load image data (e.g., CT or MRI). The controller 110 may window/crop the image data to the neighborhood near the organ of interest (e.g., L5 of lumber spine for spine surgery). The controller 110 may perform segmentation medical image data (e.g., CT or MRI) to isolate the organ of interest (e.g., L5 or lumber spine for spine surgery.) The controller 110 may reduce the image data into surface data of organ of interest (e.g., surface of L5 of lumber spine). The controller 110 may perform surface-based image registration between the surface data of organ of interest and the intraoperative 3D scan.

In one embodiment, the intraoperative 3D scan is spatially filtered or trimmed. Therefore, only a subset of the intraoperative 3D scan is used for surface-based registration. The spatial filtering may be manual, automatic, or a combination thereof. In one example, the spatial filtering is conducted per each vertebral level (L3, L4, L5). In another embodiment, the data density of the intraoperative 3D scan is adjusted. In one example, the point cloud representation of the intraoperative 3D scan is down-sampled. In yet another embodiment, the intraoperative 3D scan and medical image data are aligned with user input, prior to the surface-based registration. The user identifies and labelled a plurality of common landmarks on the intraoperative 3D scan and the medical image data. The intraoperative 3D scan and the medical image data are subsequently registered based on those landmarks. Thus, the intraoperative 3D scan and medical image data are aligned with user input and landmark based registration, prior to the surface-based registration.

Different segmentation methods may be used. In one aspect, thresholding-based segmentation may be performed. For example, global thresholding may be implemented for segmentation. In another example, adaptive thresholding may be implemented for segmentation. In another example, segmentation may be performed based on statistical shape models (SSM). In another example, segmentation may be performed based on adaptive contouring. In yet another example, segmentation may be performed based on machine learning such as artificial neural network, gradient boosting, or random forests. In another example, the segmentation may be manual. Other segmentation methods that may be applied are: Clustering methods. Motion & Interactive Segmentation, Compression-based methods, Histogram-based methods, Edge detection, Dual clustering method, Region-growing methods, Partial differential equation-based methods, Variational methods, Graph partitioning methods (e.g Markov random fields (MRF), Supervised image segmentation using MRF, Optimization algorithms, Iterated conditional modes/gradient descent, Simulated annealing (SA), Unsupervised image segmentation using MRF and expectation maximization, etc), Watershed transformation, Model-based segmentation, Multi-scale segmentation, One-dimensional hierarchical signal segmentation, Image segmentation and primal sketch, Semi-automatic segmentation, Trainable segmentation, and combination thereof.

In another embodiment, a feature-based image registration algorithm may be implemented for image registration. A feature detection algorithm may be used. In one example, scale-invariant feature transform (SIFT) is used for feature-based registration. In another example, speeded up robust features (SURF) is used for feature-based registration. In another example, Gradient Location and Orientation Histogram is used for featured-based registration. In yet another example, histogram of oriented gradients (HOG) is used for featured-based registration. It should be appreciated that feature-based image registration algorithm may be implemented on 3D point cloud or polygon meshes.

In one example, landmark based registration is implemented. The landmark may be anatomical or geometrical. For instance, a blood vessel or part of a bone may be used for landmark for registration. In another example, fluorescence tissues (e.g. tumors or blood vessels) may be used as landmark based registration. In another example, segmentation-based registration is implemented. Rigid models (e.g. points, curves, surfaces, etc) or deformable models (e.g. snakes, nets, etc) may be implemented.

In another example, fiducial based registration may be implemented. For instance, stereotactic frame, screw markers, mould, frame, dental adapter, skin markers may be used as fiducials. In another example, machine learning algorithms are used for image registration. In one aspect, supervised learning may be implemented. In another aspect, unsupervised learning may be implemented. In yet another aspect, reinforcement learning may be implemented. It should be appreciated that feature learning, sparse dictionary learning, anomaly detection, association rules may also be implemented. Various models may be implemented for machine learning. In one aspect, artificial neural networks are used. In another aspect, decision trees are used. In yet another aspect, support vector machines are used. In yet another aspect, Bayesian networks are used. In yet another aspect, genetic algorithms are used.

Figure 6A:
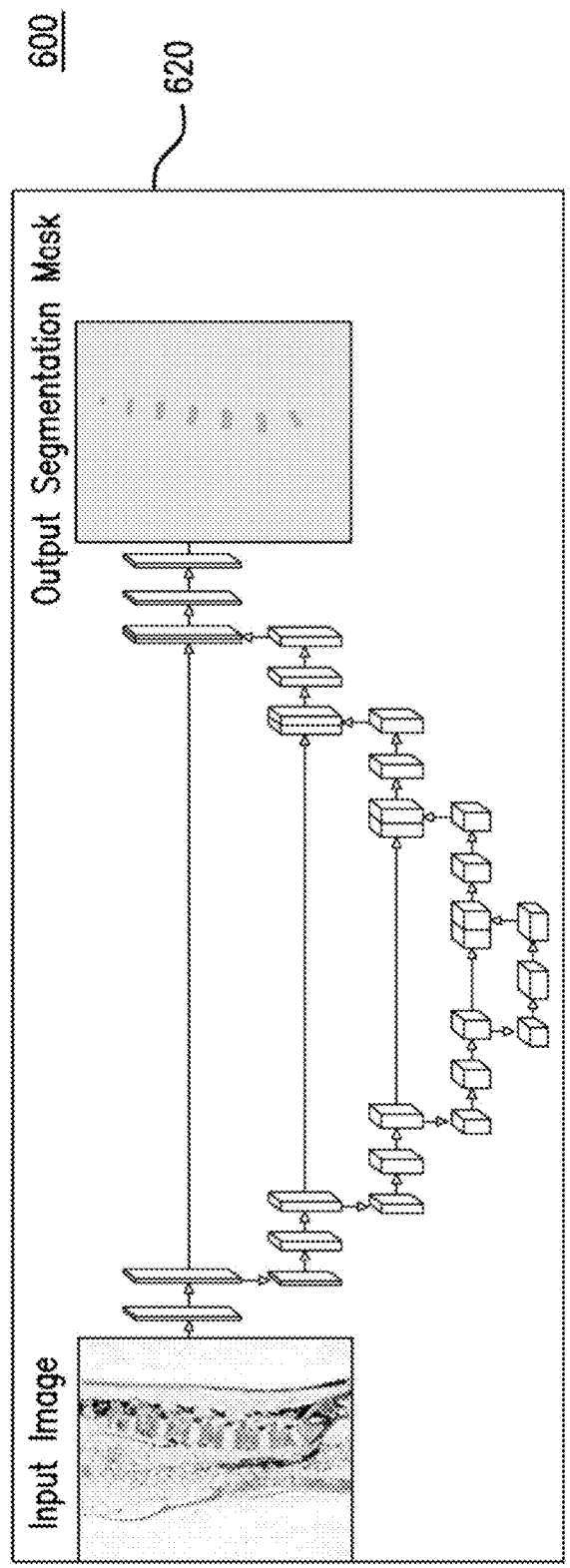
FIG. 6A illustrates a schematic view of an example of U-net architecture.

In yet another example, neural networks, convolutional neural networks, or deep learning are used for image segmentation, image registration, or a combination thereof. Neural network based systems are advantageous in many cases for image segmentation, recognition and registration tasks. A convolutional neural network configuration 600 is depicted in FIG. 6A. In one example, Supervised Transformation Estimation is implemented; In another example, Unsupervised Transformation Estimation is implemented; In yet another example, Reinforcement Learning based Registration is implemented; In yet another example, Deep Similarity based Registration is implemented. In one example, U-net is implemented for image segmentation to isolate the organ or tissue of interest (e.g. vertebral bodies). An example of U-net architecture 620 is shown in FIG. 6A.

In one example, U-Net 620 has a contraction path and expansion path. The contraction path has consecutive convolutional layers and max-pooling layer. The expansion path performs up-conversion and may have convolutional layers. The convolutional layer(s) prior to the output maps the feature vector to the required number of target classes in the final segmentation output. In one example, V-net is implemented for image segmentation to isolate the organ or tissue of interest (e.g. vertebral bodies). In one example, Autoencoder based Deep Learning Architecture is used for image segmentation to isolate the organ or tissue of interest. In one example, backpropagation is used for training the neural networks.

In yet another example, deep residual learning is performed for image recognition or image segmentation, or image registration. A residual learning framework is utilized to ease the training of networks. A plurality of layers is implemented as learning residual functions with reference to the layer inputs, instead of learning unreferenced functions. One example of network that performs deep residual learning is deep Residual Network or ResNet.

Figure 6B:
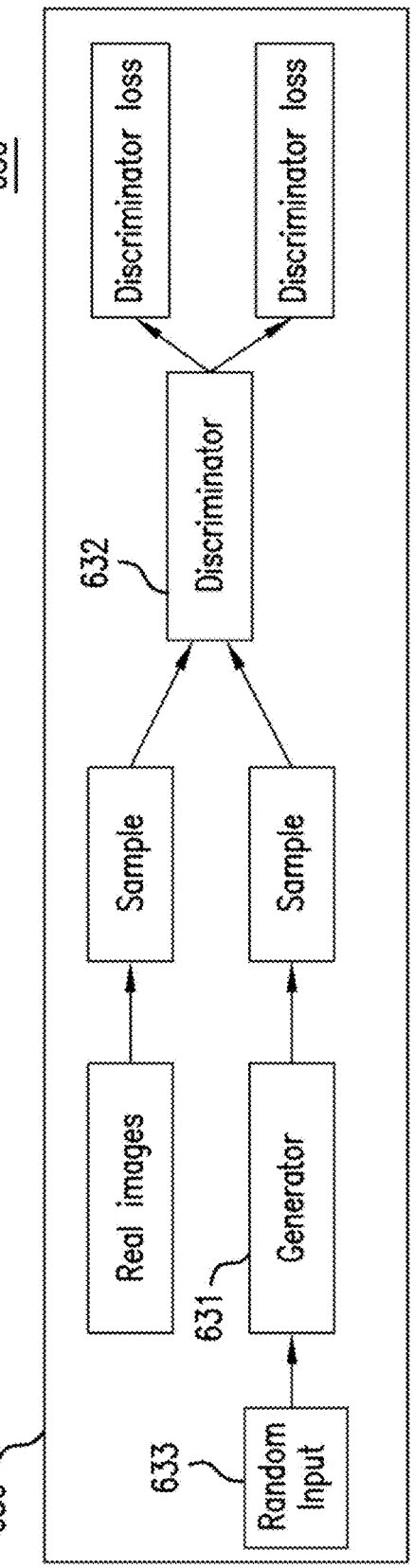
FIG. 6B illustrates a schematic view of an example of GAN configuration.

In another embodiment, a Generative Adversarial Network (GAN) is used for image recognition or image segmentation, or image registration. An example of GAN configuration 650 is shown in FIG. 6B. In one example, the GAN 630 performs image segmentation to isolate the organ or tissue of interest. In the GAN 630, a generator 631 is implemented through neural network to models a transform function which takes in a random variable 633 as input and follows the targeted distribution when trained. A discriminator 632 is implemented through another neural network simultaneously to distinguish between generated data and true data. In one example, the first network tries to maximize the final classification error between generated data and true data while the second network attempts to minimize the same error. Both networks may improve after iterations of the training process.

In yet another example, ensemble methods are used, wherein multiple learning algorithms are used to obtain better predictive performance. In one aspect, Bayes optimal classifier is used. In another aspect, bootstrap aggregating is used. In yet another aspect, boosting is used. In yet another aspect, Bayesian parameter averaging is used. In yet another example, Bayesian model combination is used. In yet another example, bucket of models is used. In yet another example, stacking is used. In yet another aspect, a random forests algorithm is used. In yet another aspect, an gradient boosting algorithm is used.

The 3D scanning controller 150 may acquire the intraoperative 3D scan of the surgical field. The controller 110 may load image data (e.g., CT or MRI). The controller 110 may perform segmentation on the medical image data (e.g., CT or MRI) to isolate the organ of interest (e.g., L5 of lumber spine for spine surgery. The controller 110 may reduce the image data into surface data of the organ of interest (e.g., surface of L5 of lumber spine). The controller 110 may use surface data of the organ of interest to perform surface-based image registration with the intraoperative 3D scan. The image registration uses a machine learning algorithm.

Tracker and Tracking Controller:

The tracker 130 can track the surgical tools. The tracking controller 140 controls how the tracker 130 tracks the surgical tools. The tracking may be enabled via optical tracking, or electromagnetic tracking, or a combination thereof. In one aspect, the tracker 130 is an optical tracker. In another aspect, the tracker 130 is an electromagnetic tracker.

In one embodiment, the optical tracking is implemented through a plurality of reflective markers. The reflective marker may be a sphere, plates or other structures that are highly reflective. In another embodiment, the optical tracking is implemented through a plurality of light emitting diodes (LEDs). The LEDs may be in the near infrared spectrum to enable accurate tracking. In one aspect, active markers such as LEDs may be attached to one end of surgical tools, to locate their locations. NDI Optotrak systems are examples of optical tracking systems that may be used for this embodiment.

In another embodiment, a modulated infrared optical tracking method may be utilized by the system. As such, the wavelength of the optical emitters for tracking purposes (such as LEDs) may be different from the wavelength used by the 3D scanner and the wavelengths used for the intraoperative imaging. Methods, such as spectral filtering may be used to facilitate the separation of wavelengths between the optical emitter from the tracker 130 from other signals. In another example, frequency modulation may also be used to separate the signal from the tracking optical emitters from background signals. Specifically, frequency filters may be used to separate the tracking signals.

In another example, the tracker 130 comprises an inertial measurement unit (IMU). In one aspect, the IMU has a combination of accelerometers and gyroscopes, and optionally magnetometers. Therefore, gyroscopic tracking may be performed. In one aspect, the IMU may be attached to the patient or a surgical tool. In another embodiment, video tracking may be performed based on computer vision. Various object tracking algorithms may be implemented. In one aspect, optical flow algorithm is used for video tracking. If electromagnetic tracking is used, the tracker 130 may incorporate small coils or similar electromagnetic field sensors and multiple position measurement devices. The electromagnetic field sensors may be attached to the surgical tools and the patient, to locate their locations, respectively.

In one example, the tracing controller 140 first registers the preoperative image data (preoperative or intraoperative CT or MRI) with the intraoperative image data (e.g. 3D scan of the anatomy obtained by the system); the tracking controller 140 subsequently tracking the registration optically using a reference frame with reflective markers. Because the reference frame has a fixed location with respect to the patient, tracking the reference frame (e.g. a Mayfield clamp with markers) can enable accurate tracking of the registration. In addition, surgical tools with markers/fiducials can also be tracked by the tracker 130. Therefore, the relationship between the surgical tool and the registration can established via the reference frame. The tracking controller 140 controls how the tracker 130 tracks the surgical tools and other objects. It should be appreciated that the tracker 130 may share common hardware with other components of the systems. In one example, the 3D scanner already enable optical tracking; therefore, no standalone tracker 130 is needed. In another example, the imaging detector 180 already enable optical tracking; therefore, no standalone tracker is needed.

Display

The display 120 may be a digital or analog display for display the medical information to the user. In one embodiment, the display 120 is a flat panel 2D monitor or TV. In another embodiment, the display 120 is a flat panel 3D monitor or 3D TV. The 3D monitor/TV may need to work with passive polarizers or active shutter glasses. In one aspect, the 3D monitor/TV is glass-free. It should be appreciated that the display 120 may be a touchscreen, or a projector. In one example, the display 120 comprises a half transparent mirror that can reflect projection of images to the eyes of the user. The images being projected may be 3D, and the user may wear 3D glasses (e.g. polarizer; active shutter 3D glasses) to visualize the 3D image data reflected by the half transparent mirror. The half transparent mirror may be placed on top of the surgical field to allow the user to see through the half transparent mirror to visualize the surgical field.

In another embodiment, the display 120 is a near-eye display. It should be appreciated that the near eye may be 3D. It should be further appreciated that the near-eye display 120 may comprise LCD (liquid crystal) microdisplays, LED (light emitting diode) microdisplays, organic LED (OLED) microdisplays, liquid crystal on silicon (LCOS) microdisplays, retinal scanning displays, virtual retinal displays, optical see through displays, video see through displays, convertible video-optical see through displays, wearable projection displays, projection display, and the like. It should be the appreciated that the display 120 may be stereoscopic to enable displaying of 3D content. In another embodiment, the display 120 is a projection display.

In one aspect, the display 120 is a digital 3D magnification device capable of enable different magnification levels at different levels. In another aspect, the display 120 is an augmented reality (AR) display that can display the surgical navigation and imaging data as part of the AR content. The display 120 can display the 3D scanning data, registration data, navigation data, original preoperative image data, intraoperative image data, or a combination thereof, to the user. In one aspect, the display 120 can display the registration process, positions of surgical tools, and tracking of registration. In another aspect, the display may display intraoperative imaging data such as color imaging or fluorescence imaging data.

Controller

The controller 110 comprises the hardware and software necessary to implement the aforementioned methods. In one embodiment, the controller 110 involves a computer-readable medium comprising processor-executable instructions configured to implement one or more of the techniques presented herein. An example embodiment of a computer-readable medium or a computer-readable device comprises a computer-readable medium, such as a SSD, CD-R, DVD-R, flash drive, a platter of a hard disk drive, etc., on which is encoded computer-readable data. This computer-readable data, such as binary data comprising at least one of a zero or a one, in turn comprises a set of computer instructions configured to operate according to one or more of the principles set forth herein. In some embodiments, the set of computer instructions are configured to perform a method, such as at least some of the exemplary methods described herein, for example. In some embodiments, the set of computer instructions are configured to implement a system, such as at least some of the exemplary systems described herein, for example. Many such computer-readable media are devised by those of ordinary skill in the art that are configured to operate in accordance with the techniques presented herein.

The following discussion provide a brief, general description of a suitable computing environment to implement embodiments of one or more of the provisions set forth herein. Example computing devices include, but are not limited to, personal computers that may comprise a graphics processing unit (GPU), server computers, hand-held or laptop devices, mobile devices (such as mobile phones, Personal Digital Assistants (PDAs), media players, and the like), multiprocessor systems, consumer electronics, mini computers, mainframe computers, a microcontroller, a Field Programmable Gate Array (FPGA), an application-specific integrated circuit (ASIC), distributed computing environments that include any of the above systems or devices, and the like.

Although not required, embodiments are described in the general context of "computer readable instructions" being executed by one or more computing devices. Computer readable instructions may be distributed via computer readable media. Computer readable instructions may be implemented as program components, such as functions, objects, Application Programming Interfaces (APIs), data structures, and the like, that perform particular tasks or implement particular abstract data types. Typically, the functionality of the computer readable instructions may be combined or distributed as desired in various environments.

In one example, a system comprises a computing device configured to implement one or more embodiments provided herein. In one configuration, the computing device includes at least one processing unit and one memory unit. Depending on the exact configuration and type of computing device, the memory unit may be volatile (such as RAM, for example), non-volatile (such as ROM, flash memory, etc., for example) or some combination of the two. In other embodiments, the computing device may include additional features and/or functionality. For example, the computing device may also include additional storage (e.g., removable and/or non-removable) including, but not limited to, cloud storage, magnetic storage, optical storage, and the like. In one embodiment, computer readable instructions to implement one or more embodiments provided herein may be in the storage. The storage may also store other computer readable instructions to implement an operating system, an application program, and the like. Computer readable instructions may be loaded in the memory for execution by the processing unit, for example.

The term "computer readable media" as used herein includes computer storage media. Computer storage media includes volatile and nonvolatile, removable and non-removable media implemented in any method or technology for storage of information such as computer readable instructions or other data. Computer storage media includes, but is not limited to, RAM, ROM, EEPROM, flash memory or other memory technology, CD-ROM, Digital Versatile Disks (DVDs) or other optical storage, magnetic disk storage or other magnetic storage devices, or any other medium which may be used to store the desired information and which may be accessed by computing device.

The computing device may also include communication connection(s) that allows the computing device to communicate with other devices. Communication connection(s) may include, but is not limited to, a modem, a Network Interface Card (NIC), an integrated network interface, a radio frequency transmitter/receiver, an infrared port, a USB connection, or other interfaces for connecting computing device to other computing devices. Communication connection(s) may include a wired connection or a wireless connection. Communication connection(s) may transmit and/or receive communication media.

The computing device may include input device(s) such as keyboard, mouse, pen, voice input device, touch input device, infrared cameras, depth cameras, touchscreens, video input devices, and/or any other input device. Output device(s) such as one or more displays, speakers, printers, and/or any other output device may also be included in the computing device. Input device(s) and output device(s) may be connected to the computing device via a wired connection, wireless connection, or any combination thereof. In one embodiment, an input device or an output device from another computing device may be used as input device(s) or output device(s) for computing device.

Components of computing device 6712 may be connected by various interconnects, such as a bus. Such interconnects may include a Peripheral Component Interconnect (PCI), such as PCI Express, a Universal Serial Bus (USB), firewire (IEEE 1394), an optical bus structure, and the like. In another embodiment, components of computing device may be interconnected by a network. For example, the memory may be comprised of multiple physical memory units located in different physical locations interconnected by a network.

Those skilled in the art will realize that storage devices utilized to store computer readable instructions may be distributed across a network. For example, a computing device accessible via a network may store computer readable instructions to implement one or more embodiments provided herein. Computing device may access another computing device and download a part or all of the computer readable instructions for execution. Alternatively, the first computing device may download pieces of the computer readable instructions, as needed, or some instructions may be executed at the first computing device and some at the second computing device.

Various operations of embodiments are provided herein. In one embodiment, one or more of the operations described may constitute computer readable instructions stored on one or more computer readable media, which if executed by a computing device, will cause the computing device to perform the operations described. The order in which some or all of the operations are described should not be construed as to imply that these operations are necessarily order dependent. Alternative ordering will be appreciated by one skilled in the art having the benefit of this description. Further, it will be understood that not all operations are necessarily present in each embodiment provided herein. Also, it will be understood that not all operations are necessary in some embodiments.

It should be appreciated that the controller 110, the tracking controller 140, the light source controller 190, the intraoperative imaging controller 170, and the 3D scanning controller 150 may share common hardware and software with the other components of the systems. In one example, the controller 110 has necessary hardware to run the software to control the 3D scanner 160; therefore, no standalone 3D scanning controller 150 is necessary. In another example, the controller has necessary hardware to run the software to control the imaging detector 180; therefore, no standalone intraoperative imaging controller 170 is necessary. In yet another example, the controller 110 has necessary hardware to run the software to control the light source 195; therefore, no standalone light source controller 190 is necessary. In yet another example, the controller has necessary hardware to run the software to control the tracker 130; therefore, no standalone tracking controller 140 is necessary.

Systems with Master-Slave Dual 3D Scanners

Figure 7:
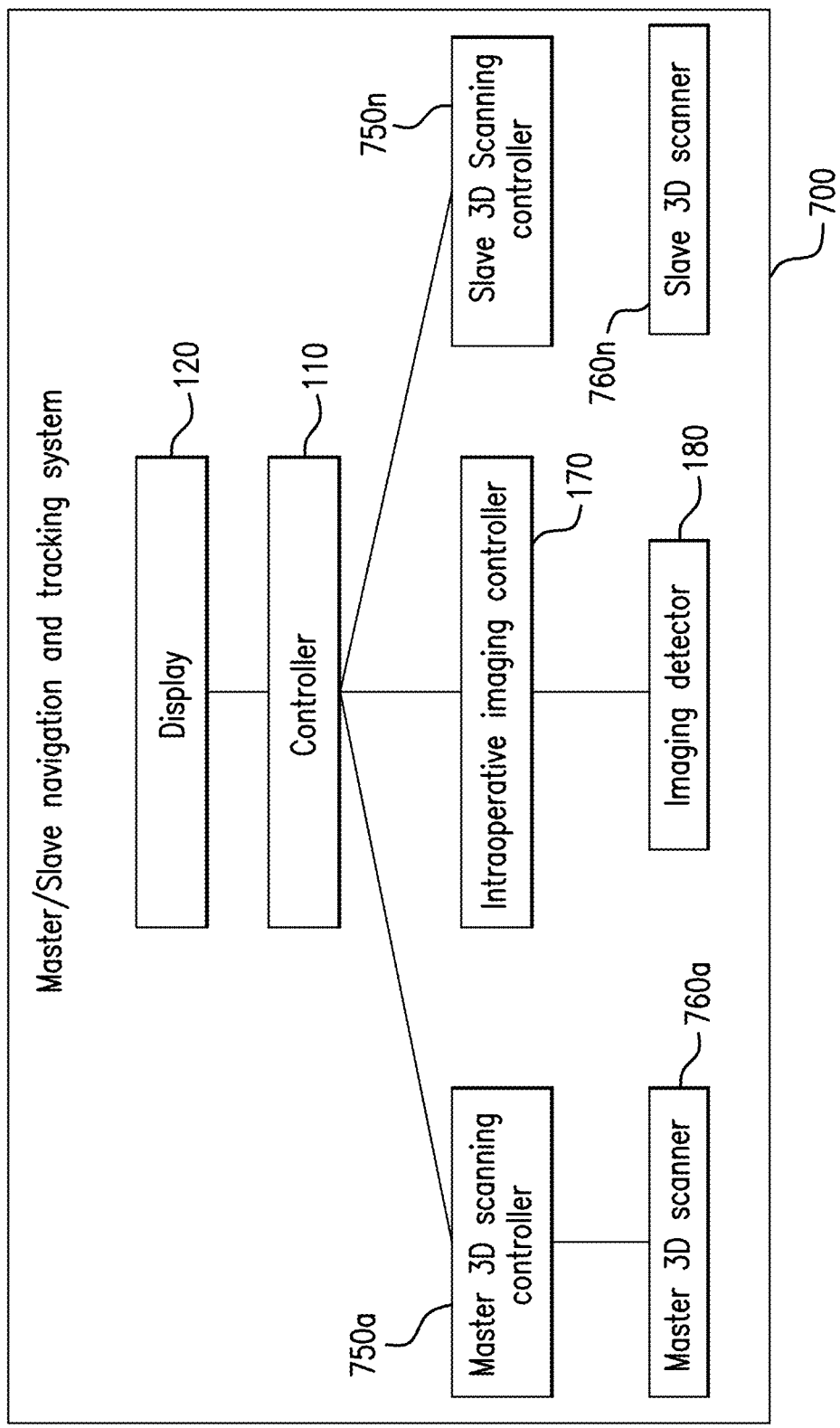
FIG. 7 illustrates a block diagram of a master-slave system with more than one 3D scanners.

In one embodiment, the system 700 comprises more than one 3D scanners, as shown in FIG. 7. In this invention, we denote the first 3D scanner as the master 3D scanner 760*a*, and the second 3D scanner as the slave 3D scanner 760*n*. In one aspect, the system further comprises a first 3D scanning controller, denoted as the master 3D scanning controller 750*a*. The master 3D scanning controller 750*a* controls the master 3D scanner 760*a* to perform the 3D scan on organs and patients. In another aspect, the system 700 further comprises a second 3D scanning controller, denoted as the slave 3D scanning controller 750*n*. The slave 3D scanning controller 750*n* controls the slave 3D scanner 760*n* to perform the 3D scan on organs and patients. It should be appreciated that the master 3D scanning controller 750*a* and slave 3D scanning controller 750*n* may be embodied as one single circuit, one single microcontroller, or one single computer that controls both master 3D scanner 760*a* and slave 3D scanner 760*n* to perform 3D scans.

In one aspect, the system further comprises an intraoperative imaging controller 170 and an imaging detector 180. In one embodiment, the master 3D scanner 760*a* comprises a pattern creator. In one example, the pattern creator comprises at least one digital micromirror device (DMD), and said digital micromirror device are controlled by the 3D scanning controller to create patterns for 3D scanning. An instance of such a pattern creator is Texas Instruments DLP products. In another example, the pattern creator comprises at least one light emitting diode, at least one lens, and at least one thin-film-transistor liquid-crystal display, and said light emitting diode and said thin-film-transistor liquid-crystal display are controlled by the master 3D scanning controller 750*a* to create patterns for intraoperative 3D scanning.

In another embodiment, the master 3D scanner 760*a* comprises a statistical pattern creator, wherein the statistical pattern creator creates random patterns or pseudo-random patterns and said patterns are projected to the patient to facilitate the 3D scanning of patient anatomy. In one aspect, the statistical pattern creator may create dynamic statistical patterns that changes temporarily. In another embodiment, the master 3D scanner 760*a* comprises a non-statistical pattern creator, wherein the non-statistical pattern creator creates non-statistical patterns are projected to the patient to facilitate the 3D scanning of patient anatomy. In one aspect, the non-statistical pattern is binary code, stripe boundary code, or sinusoidal code. It should be appreciated that all the non-statistical pattern described previously may be applied here.

In one aspect, the slave 3D scanner 760*n* uses similar components as the master 3D scanner 760*a*. For instance, both master 3D scanner 760*a* and slave 3D scanner 760*n* may use DMDs. In some cases, the master 3D scanner 760*a* and the slave 3D scanner 760*n* are the same, hardware wise. In one example, the master 3D scanner 760*a* and the slave 3D scanner 760*n* share a single pattern creator that creates dynamic projection patterns. The pattern creator may be a statistical pattern creator or a non-statistical pattern creator. The camera in the master 3D scanner 760*a* and the camera in the slave 3D scanner 760*n* may be similar or the same. Thus, the master 3D scanner 760*a* and the slave 3D scanner 760*n* together has only one pattern creator but two cameras. In one example, the pattern creator is a projector.

In another aspect, the slave 3D scanner 760*n* uses different components from components of the master 3D scanner 760*a*. In one example, the master 3D scanner 760*a* uses DMDs, but the slave 3D scanner 760*n* has a statistical pattern creator that creates random patterns or pseudo-random patterns. In another example, the master 3D scanner 760*a* uses liquid-crystal display, but the slave 3D scanner 760*n* has a statistical pattern creator that creates random patterns or pseudo-random patterns. In one aspect, the master 3D scanner 760*a* performs 3D scan of patients with higher resolution and slower speed, and the slave 3D scanner 760*n* performs 3D scan of patients with lower resolution and faster speed. This is advantageous in many cases. For example, the master 3D scanner 760*a* can create a high resolution 3D scan at the beginning of surgery (master 3D scan), and be idle afterwards; the slave 3D scanner 760*n* can continuously scan patient with a lower resolution 3D scan at high speed (slave 3D scan(s)). The system can use slave 3D scan(s) to monitor the patient and registration status. For example, if significant changes in surgical landscape is detected automatically, the system can use the master 3D scanner 760*a* to generate an updated master 3D scan for image registration and navigation. In another example, the user can control the system to use the master 3D scanner 760*a* to generate master 3D scan on demand. In another example, the master 3D scanner 760*a* captures a 3D scan with a bigger field of view (FOV), and the slave 3D scanner 760*n* captures a 3D scan with a smaller field of view. Both the master 3D scan (bigger FOV) and slave 3D scan (smaller FOV) may be used for image registration.

The master 3D scanner 760*a* and slave 3D scanner 760*n* can work together in several different ways. In one aspect, the master 3D scanner 760*a* and slave 3D scanner 760*n* can perform 3D scanning concurrently, controlled by the master 3D scanning controller 750*a* and the slave 3D scanning controller 750*n*, respectively. In another aspect, the master 3D scanner 760*a* and slave 3D scanner 760*n* can perform 3D scanning sequentially, controlled by the master 3D scanning controller 750*a* and the slave 3D scanning controller 750*n*, respectively. The sequential master 3D scan and slave 3D scan can minimize the crosstalk between master 3D scanner 760*a* and slave 3D scanner 760*n*. For instance, the system performs master 3D scan first using the master 3D scanner 760*a*, and subsequently performs slave 3D scan using the slave 3D scanner 760*n*.

In another aspect, the master 3D scanner 760*a* and slave 3D scanner 760*n* can perform 3D scanning in an interleaved fashion, controlled by the master 3D scanning controller 750*a* and slave 3D scanning controller 750*n*, respectively. For instance, the system performs a first half of master 3D scan; the system secondly performs a first half of slave 3D scan; thirdly, the system performs the second half of master 3D scan, and the master 3D scan is completed; lastly, the system performs the second half of slave 3D scan, and the slave 3D scan is completed. It should be appreciated there are many ways to interleave the master 3D scan and slave 3D scan; in one aspect, the master 3D scan is divided into a plurality of master 3D scan portions, and the slave 3D scan is divided into a plurality of slave 3D scan portions. The master 3D scan portions and slave 3D scan portions are acquired in an interleaved fashion. An example of temporal sequence is: master 3D scan portion 1, slave 3D scan portion 1, master 3D scan portion 2, slave 3D scan portion 2, master 3D scan portion 3, slave 3D scan portion 3, etc.

The master 3D scanner 760*a* may capture a master 3D scan of an anatomy of a patient. The slave 3D scanner 760*n* may capture a slave 3D scan of an anatomy of a patient. The controller 110 may register the slave 3D scan to the master 3D scan to generate a co-registered intraoperative 3D scan. The controller 110 may load medical image data (e.g., CT or MRI). The controller 110 may perform segmentation on the medical image data (e.g., CT or MRI) to isolate the organ of interest (e.g., L5 of lumber spine for spine surgery). The controller 110 may reduce the image data into the surface data of the organ of interest (e.g., surface of L5 of lumber spine). The controller 110 may perform surface-based image registration between the surface data of the organ of interest and the intraoperative 3D scan. The display 120 may display the results of the surface-based image registration to the user.

In one embodiment, the master 3D scanner 760*a* is a part of a surgical navigation system, and the slave 3D scanner 760*n* is a part of a surgical tool, such as surgical drill. In another embodiment, there are a plurality of slave 3D scanners 760*n*. For instance, more than one surgical tools each with a slave 3D scanner 760*n* can work together. In another embodiment, there are a plurality of master 3D scanners 760*a*. In one aspect, the master 3D scanner 760*a* is positioned further away from the patient, and the slave 3D scanner 760*n* is positioned closer to the patient. In another aspect, the master 3D scanner 760*a* is positioned at a first angle relative to the patient, and the slave 3D scanner 760*n* is positioned at a second angle relative to the patient. Different angles relative to patient and different distances from patient can help the system to capture 3D scans without blind spots due to obstruction of line of sight by obstacles such as surgical instruments and surgeon's arms.

In another embodiment, the system further comprises a tracker and a tracking controller, in addition to the other components shown in FIG. 7. The image registration may be passed to the tracking controller and tracker, and the tracker can track at least one object such as a surgical tool. In one example, the tracker uses optical tracking, such as passive infrared tracking based on reflective spheres attached to the surgical tools. In another example, the tracker uses electro-magnetic tracking. The master 3D scanner 760*a* may capture a master 3D scan of an anatomy of a patient. The Slave 3D scanner 760*n* may scan an anatomy of a patient. The controller 110 may register the slave 3D scan to the master 3D scan to generate a co-registered intraoperative 3D scan. The controller 110 may load medical image data (e.g., CT or MRI). The controller 110 may perform segmentation of medical image data (e.g, CT or MRI) to isolate the organ of interest (e.g., L5 of lumber spine for spine surgery). The controller 110 may reduce the image data into the surface data of the organ of interest (e.g., surface of L5 of lumber spine). The controller 110 may perform surface-based image registration between the surface data of the organ of interest and the intraoperative 3D scan. The tracker may track positions of at least one entity in a surgery.

Smart Surgical Instruments with Navigation Capability

Figure 8:
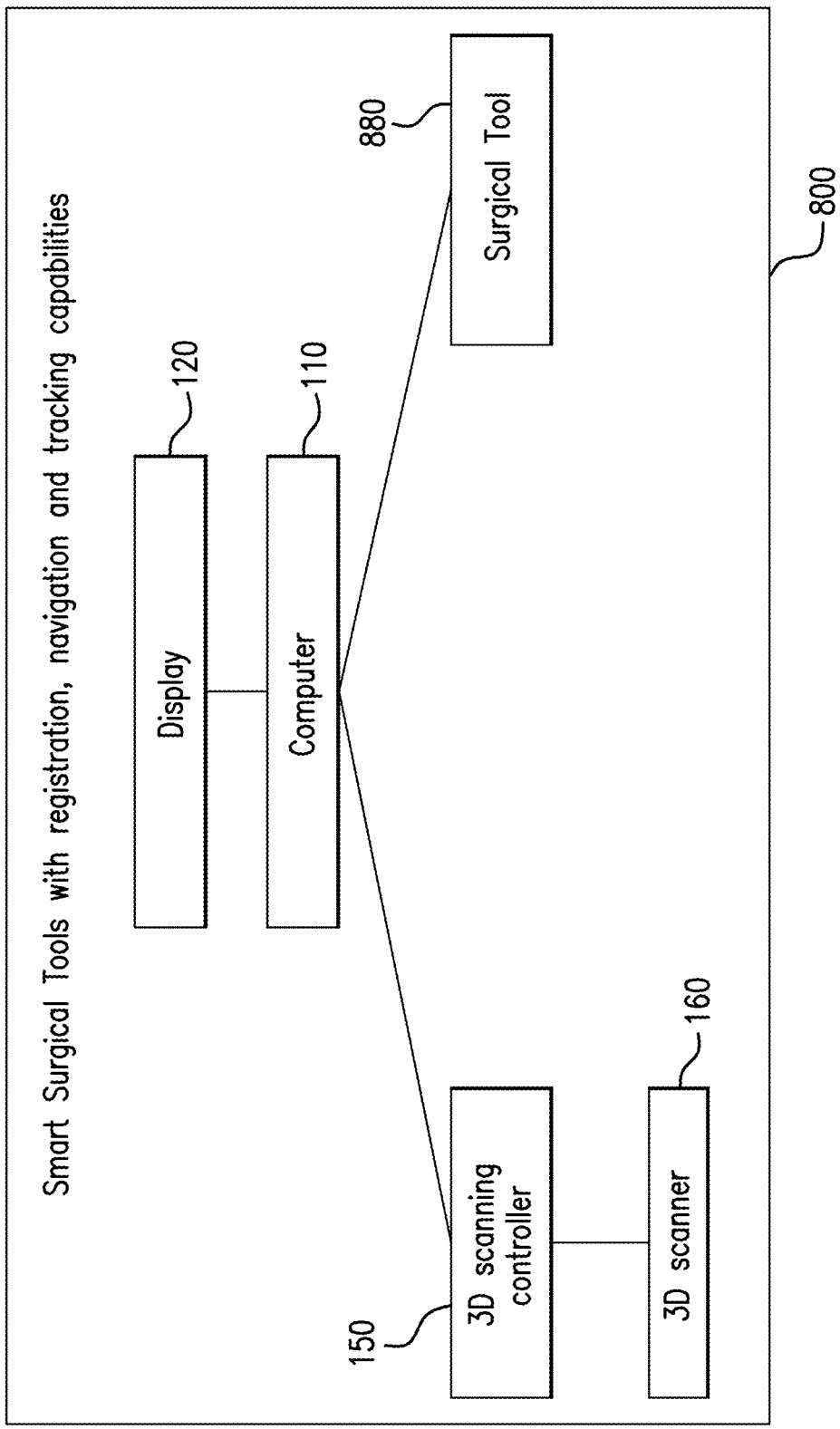
FIG. 8 illustrates a block diagram of a 3D scanning controller and a 3D scanner that interacts with a surgical tool.

In one embodiment, the system 800 comprises a 3D scanning controller 150, a 3D scanner 160, and a surgical tool 880, as shown in FIG. 8. The 3D scanning controller 150 controls the 3D scanner 160 to capture an intraoperative 3D scan, and the intraoperative 3D scan may be used for image registration and navigation. The image navigation can guide the placement of the surgical tools such as a drill or saw. In one aspect, the system 800 further comprises a controller 110 and a display 120. The controller 110 can perform the image registration process using an image registration algorithm, and the display 120 can display the image registration and navigation data to the user. In one aspect, the display 120 is an LCD display or an OLED display attached to the surgical tool.

Figure 9:
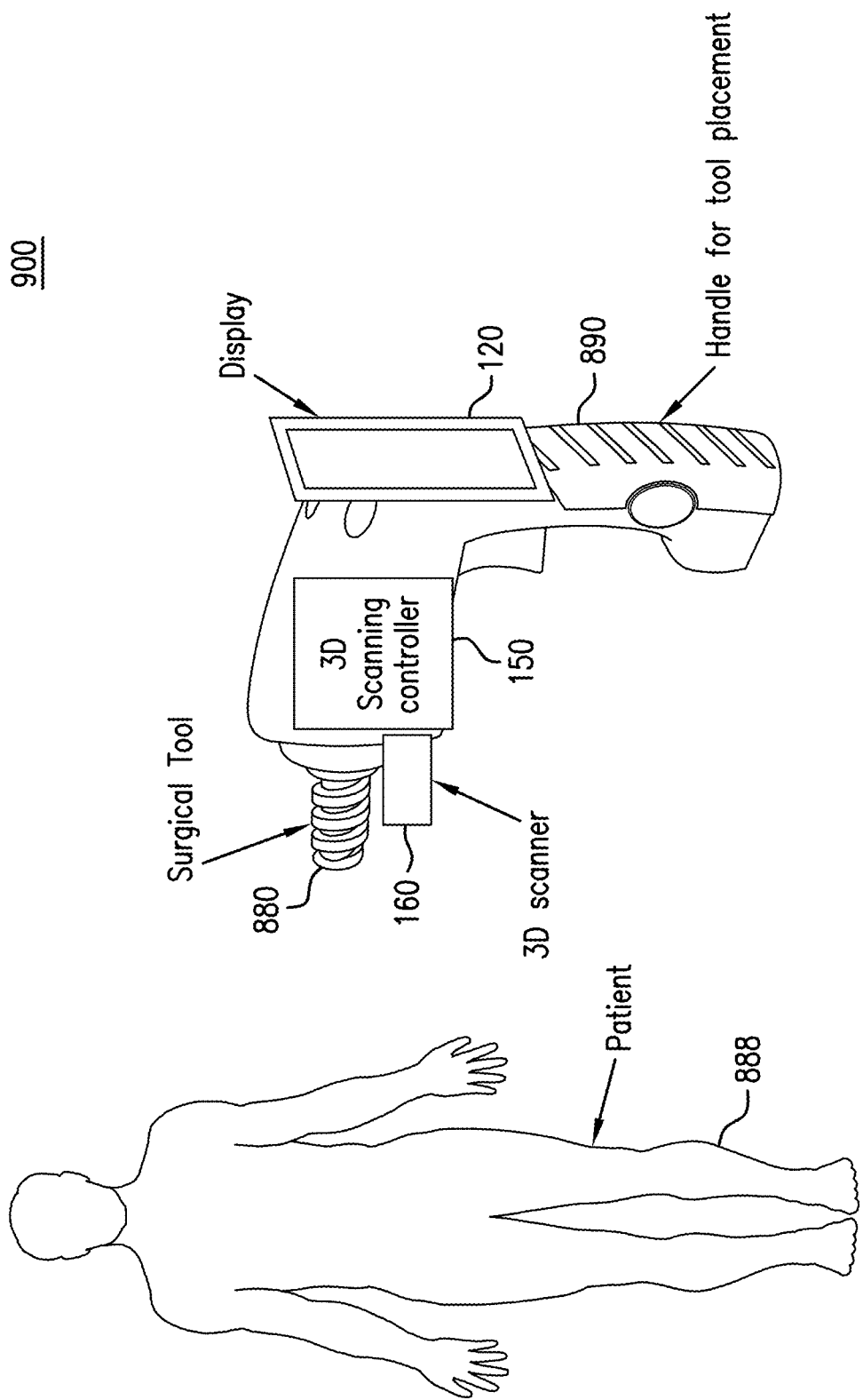
FIG. 9 illustrates a schematic view of a 3D scanner that is situated at the end of the smart surgical tool closer to the patient and the display is situated at the end of the smart surgical tool closer the user/surgeon.

In one embodiment, the 3D scanner 160 is situated at the end of the smart surgical tool 880 closer the patient, and the display 120 is situated at the end of the smart surgical tool 880 closer the user/surgeon as shown in the surgical tool configuration 900 depicted in FIG. 9. Therefore, the 3D scanner 160 can capture a 3D scan of the patient 888 without obstruction of the surgical tool 880, and the display 120 can display the surgical navigation and registration data to the user easily. In one aspect, the smart surgical tool 880 includes a handle 890 so that it may be handheld by the user. In another aspect, the smart surgical tool 880 is mounted on a mechanical arm that may be positioned manually or robotically. It should be appreciated that the smart surgical tool 880 may be very small and light weight.

In one embodiment, the smart surgical tool 880 comprises a surgical instrument. Here are some examples of instruments that may be integrated as part of the smart surgical tool 880: graspers, forceps, clamps, occluders, needle drivers, retractors, distractors, positioners, stereotactic devices, mechanical cutters, scalpels, lancets, drill bits, rasps, trocars, ligasure, harmonic scalpel, surgical scissors, rongeurs, dilators, specula, suction tips, tubes, sealing devices, surgical staplers, irrigation and injection needles, tips and tubes, powered devices, drills, saws, dermatomes, scopes, probes, endoscopes, tactile probes, ultrasound tissue disruptors, cryotomes, cutting laser guides, measurement devices, etc.

In one embodiment, the instrument/tool in the smart surgical tool 880 may be replaced with other compatible surgical tools and instruments. For example, a lancet initially installed in the smart surgical tool 880 may be replaced with a trocar. The smart surgical tool 880 may be used a variety of surgical instruments to guide surgery. In one aspect, the smart surgical tool 880 is an attachment to any compatible surgical instrument. In one example, the system comprises an attachment mechanism for attaching surgical instruments and tools. Different surgical tools and instruments may be attached or mounted to the system using the attachment mechanism. The attachment mechanism may be mechanical, chemical, electrical, or electromagnetic. The instruments may be mounted on, installed on, screwed into, clipped to, coupled to, slide into, or pushed into the system.

In another embodiment, the smart surgical tool 880 further comprises an imaging detector and an intraoperative imaging controller. In one example, the imaging detector is a fluorescence imaging camera. In another example, the imaging detector is a color camera. Therefore, intraoperative imaging may be conducted by the smart surgical tool 880. In another example, the smart surgical tool 880 further comprises a surgical tool controller 110 that controls the surgical tool 880. In one embodiment, the imaging detector is situated at the end of the smart surgical tool 880 closer the patient 888, and the display 120 is situated at the end of the smart surgical tool 880 closer the user/surgeon. Therefore, the imaging detector can capture an intraoperative image of the patient 888 without obstruction of the surgical tool 880, and the display 120 can display the surgical imaging data to the user easily. In another embodiment, the smart surgical tool 880 comprises a robotic arm. The system 800 may be placed by the robotic arm under user's direction. The surgical tool 880 can also be trigger by the user manually or automatically (e.g. start drilling and stop drilling). The image registration and navigation data may be used to guide the placement and control of the tool and robotics.

Registration Per Individual Organ Level

In one embodiment, the registration may be performed at an individual organ level. For example, the spine navigation, registration may be generated per individual vertebrae level. For instance, for L3, L4, L5 lumber fusion procedure, the registration may be performed based on L3 vertebrae, based on L4 vertebrae, or based on L5 vertebrae, respectively. In one aspect, the system 1000 can generate different image masks (e.g. L3 mask, L4 mask, L5 mask) to spatially filter the intraoperative 3D scan data and/or preoperative CT data, for registration at different levels. For example, the system 1000 can register the intraoperative 3D scan only to the L5 CT data.

The 3D scanner 160 may acquire an intraoperative 3D scan of the surgical field. The controller 1010 may load medical image data (e.g., CT or MRI). The controller 1010 may perform segmentation of medical image data (e.g., CT or MRI) to isolate the organ of interest (e.g., L5 of lumber spine for spine surgery) and generate image mask for different organs (e.g. L3 mask, L4 mask, L5 mask). The controller 1010 may reduce the image data into surface data of the organ of interest (e.g., surface of L5 of lumber spine). The controller 1010 may use surface data of the organ of interest (e.g., surface of L5 of lumber spine) to perform surface-based image registration with intraoperative 3D scan.

After image registration based on L5 vertebra is obtained, image registration based on L4 vertebra and L3 vertebra can also be generated. All of image registrations (e.g. L3 based registration, L4 based registration, and L5 based registration) or a subset of registration (L5 based registration only) may be presented to the user. In another example, the image registration may be performed at a level including more than one organ. For example, for navigation of L3, L4, L5 fusion surgery, L3 and L4 may be used for image registration and navigation. The system 1000 can generate and an image mask including only L3 and L4 vertebrae.

Monitoring Movements of Organs

In surgical navigation, organs often move as the surgery progresses. For instance, in spine surgeries, vertebrae often move after the initial image registration is completed. The organ movement compromises the accuracy of surgical navigation. Thus, it is advantageous to monitor tissue movements after initial image registration. The 3D scanner 160 may acquire a first operative 3D scan of the surgical field (initial 3D scan). The 3D scanner 160 may acquire a second intraoperative 3D scan of the surgical field (subsequent 3D scan). The controller 1010 may compare the first intraoperative 3D scan and the second intraoperative 3D scan to calculate the intraoperative 3D scan difference. The controller 1010 may repeat organ movement when the intraoperative 3D scan difference is over the threshold.

It should be appreciated that the threshold of the intraoperative 3D scan difference may be manually set, automatically set, proportionally set (by percentage, e.g. 5%), or set using machine learning algorithms. The intraoperative 3D scans may be represented in different data structures, such as point clouds, polygon meshes, or other data structures. The controller 1010 may generate an image mask to include the organs of interest. The 3D scanner 160 may use the image mask to acquire a first intraoperative 3D scan of the surgical field (initial 3D scan). The 3D scanner 160 may use the image mask to acquire a second intraoperative 3D scan of the surgical field (subsequent 3D scan). The controller 1010 may compare the first intraoperative 3D scan and the second intraoperative 3D scan to calculate the intraoperative 3D scan difference. The controller 1010 may repeat organ movement when the intraoperative 3D scan difference is over the threshold.

In another example, the comparison between initial intraoperative 3D scan and subsequent intraoperative 3D scan is performed based on image registration between the initial intraoperative 3D scan and the subsequent intraoperative 3D scan. When there is little organ movement, the registration between initial intraoperative 3D scan and subsequent intraoperative 3D scan is good; when there is significant organ movement, the registration between initial intraoperative 3D scan and subsequent intraoperative 3D scan is worse and there is a bigger misalignment. Therefore, the system can monitor the organ movement by monitor the image registration between the initial intraoperative 3D scan and subsequent intraoperative 3D scan. In one aspect, the image registration may be conducted using surface-based image registration. In one example, the surface-based image registration may be performed using iterative closest point (ICP) method. In one aspect, the system can return a confidence level score that indicates the wellness of the registration. When the confidence score is high, less organ movement is reported; When the confidence score is low, more organ movement is reported.

The controller 1010 may generate an image mask to include the organs of interest. The 3D scanner 160 may use the image mask to acquire a first intraoperative 3D scan of the surgical field (initial 3D scan). The 3D scanner 160 may use the image mask to acquire a second intraoperative 3D scan of the surgical field (subsequent 3D scan). The controller 1010 may register the first intraoperative 3D scan to the second intraoperative 3D scan to generate an intraoperative registration confidence level using surface-based registration. The controller 1010 may report organ movement if the intraoperative registration confidence level is under a threshold.

It should be appreciated that the threshold of the intraoperative registration confidence level may be manually set, automatically set, proportionally set (by percentage, e.g. 5%), or set using machine learning algorithms. The controller 1010 may generate an image mask to include the organs of interest. The 3D scanner 160 may use the image mask to acquire a first intraoperative 3D scan of the surgical field (initial 3D scan). The controller 1010 may load medical image data (e.g., CT or MRI). The controller 1010 may perform segmentation medical image data (e.g., CT or MRI) to isolate the organ of interest (e.g., L5 or lumber spine for spine surger) and generate image mask for organs of interest (e.g., L5 mask). The controller 1010 may use image data of organs of interest to perform image registration between the initial intraoperative 3D scan and the image data. The controller 1010 may use the image mask to acquire a second intraoperative 3D scan of the surgical field (subsequent case). The controller 1010 may compare the first intraoperative 3D scan and the second intraoperative 3D scan to calculate the intraoperative 3D scan difference. The controller 1010 may report organ movement if the intraoperative 3D scan difference is over the threshold. The controller 1010 may use the image data of the organs of interest to perform image registration between subsequent intraoperative 3D scan and image data when the intraoperative 3D scan difference is over the threshold. The image registration may be surface-based, fiducial-based, landmark-based, featured-based or a combination thereof.

In another example, the image registration between CT or MRI data and intraoperative surgical field is conducted using fiducials (e.g. trackers) and intraoperative CT scans or 3D fluoroscopy. However, the organ movement is monitored using the 3D scanner 160. When there is the significant organ movement, the system 1000 notifies the user to conduct another intraoperative CT scans or 3D fluoroscopy, to re-calculate the image registration between CT or MRI data and intraoperative surgical field. The image registration may be surface-based, fiducial-based, landmark-based, featured-based or a combination thereof.

The controller 1010 may perform the intraoperative CT scans, 3D fluoroscopy, or MRIs of the patient with fiducials to calculate the image registration between image data (e.g., CT or MRI data) and intraoperative surgical field (initial fiducial-based registration). The controller 1010 may generate an image mask to include the organs of interest. The controller 1010 may use the image mask to acquire a first intraoperative 3D scan of the surgical field (initial 3D scan). The controller 1010 may use the image mask to acquire a second intraoperative 3D scan of the surgical field (subsequent 3D scan). The controller 1010 may compare the first intraoperative 3D scan and the second intraoperative 3D scan to calculate the intraoperative 3D scan difference. The controller 1010 may report organ movement when the intraoperative 3D scan difference is over the threshold. The controller 1010 may perform another intraoperative CT scan, 3D fluoroscopy or MRI to re-calculate the image registration between image data (e.g., CT or MRI data) and intraoperative surgical field (updated fiducial-based registration) when the intraoperative 3D scan difference is over the threshold.

The controller 1010 may perform intraoperative CT scans, fluoroscopy, or MRI of patient with fiducials to calculate the image registration between image data (e.g., CT or MRI data) and intraoperative surgical field (initial fiducial-based registration). The tracker 130 may track the image registration between image data and intraoperative surgical field using optical tracking or magnetic tracking (track initial fiducial-based registration). The controller 1010 may generate an image mask to include the organs of interest. The 3D scanner 160 may use the image mask to acquire a first intraoperative 3D scan of the surgical field (initial 3D scan). The 3D scanner 160 may use the image mask to acquire a second intraoperative 3D scan of the surgical field (subsequent 3D scan). The controller 1010 may compare the first intraoperative 3D scan and the second intraoperative 3D scan to calculate the intraoperative 3D scan difference. The controller 1010 may report organ movement when the intraoperative 3D scan difference is over the threshold. The controller 1010 may perform another intraoperative CT scan, 3D fluoroscopy, or MRI, to re-calculate the image registration between the image data (e.g., CT or MRI data) and intraoperative surgical field (updated fiducial-based registration) when the intraoperative 3D scan difference is over the threshold. The tracker 130 may track the image registration between image data and intraoperative surgical field using optical tracking or magnetic tracking (track updated fiducial-base registration).

The aforementioned methods of tracking organ movements may be applied to various surgical subspecialties, such as orthopedic surgeries, neurosurgeries, spine surgeries, brain surgeries, cranial-facial surgeries, cancer surgeries, plastic surgeries, general surgeries, etc. The aforementioned methods of tracking organ movements may be performed by an apparatus that includes a 3D scanner 160, a 3D scanning controller 150, and a controller 1010 that calculates intraoperative 3D scan difference. The 3D scanning controller 150 instruct the 3D scanner 160 to perform the initial intraoperative 3D scan and subsequent intraoperative 3D scan. The controller 1010 may be a computer, an ASIC, a digital circuit, an FPGA, or a combination thereof, running the algorithm to calculate intraoperative 3D scan differences.

Figure 10:
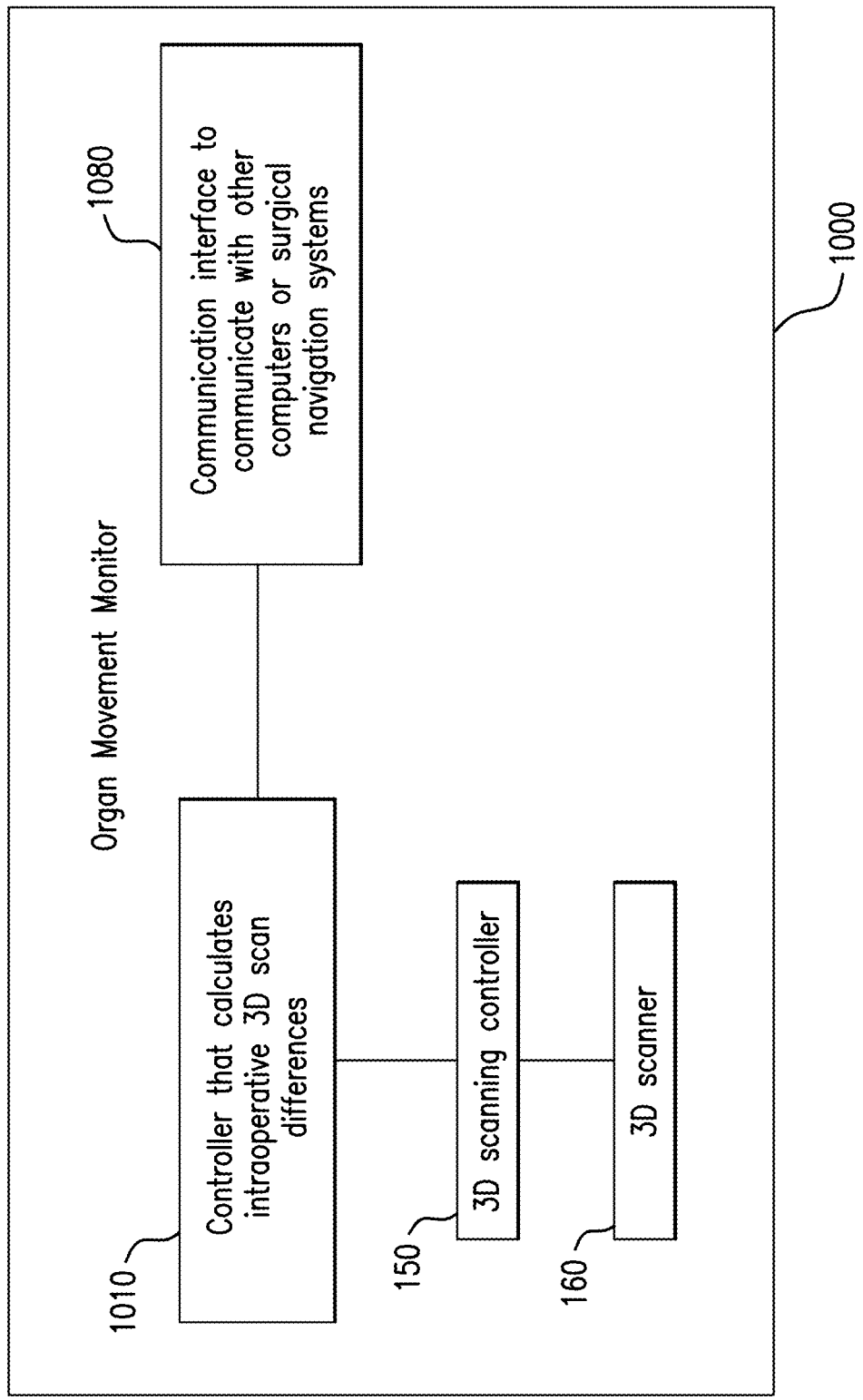
FIG. 10 illustrates a block diagram of a 3D scanning configuration that includes a communication interface that communicates with other computers or surgical navigation systems.

In another embodiment, the apparatus further comprises imaging detector 180 for intraoperative imaging, tracker for tracking fiducials 130, and light source 195 for illumination. In yet another embodiment, the apparatus 1000 comprises a communication interface 1080 with communicate with other computers or surgical navigation systems as depicted in FIG. 10. For example, when significant organ movement is detected, the apparatus 1000 notifies the other computer or surgical navigation system via the communication interface 1080 to re-calculate the image registration between CT or MRI image data and intraoperative surgical field. The communication interface 1080 may be wired or wireless.

Construct Image Mask Using Optical Properties, Thermal Properties, Tissue Properties, or Machine Learning In another embodiment, image mask may be constructed based on tissue properties. In one embodiment, the bony tissues and vascularized soft tissues are differentiated based on optical properties. In one aspect, the optical properties may be obtained using color imaging. For instance, bones tend to have different color compared to muscles or ligaments. Based on the color of tissues, bones and soft tissues may be differentiated. In another aspect, the optical properties may be obtained using hyperspectral imaging or multispectral imaging. The hyperspectral imaging data or multispectral imaging data can reveal different tissue types such as bones versus soft tissues.

In another aspect, the optical properties may be obtained using infrared reflectance imaging. The infrared reflectance imaging can reveal different tissue types, such as bones versus soft tissues. In another example, optical properties of tissues may be obtained using transmission mode optical imaging. In yet another example, optical properties of tissues such as absorption and scattering coefficient may be obtained using optical imaging. In yet another example, optical properties of tissues such as oxygen saturation may be obtained using optical imaging. In yet another example, optical properties of tissues such as polarization properties may be obtained using optical imaging. Based on optical properties of tissues, an image mask may be constructed to filter certain type of tissues (e.g. soft tissue) from the intraoperative 3D scan data. For example, an image mask may be constructed based on optical properties to filter soft tissue from the intraoperative 3D scan data, leaving only data from vertebral bodies. The filtered 3D scan data may be used for image registration and navigation, improving the registration accuracy. In another example, an image mask may be constructed based on optical properties to filter surgical tools/instruments from the intraoperative 3D scan data, leaving only data from biological tissues.

The imaging detector 180 may acquire an image of optical properties. The controller 110 may assign pixels or voxels of optical property type 1 to passband (logical level 1). The controller 110 may assign pixels or voxels of optical property type 2 to rejection band (logical level 0). Controller 110 may output an image mask based on the optical properties. In one aspect, the image mask may be used with 3D scan to obtain a spatially filtered image (e.g. using logical operation AND).

The controller 110 may use optical properties to generate an image mask to include the organs of interest and exclude tissues/organs not of interest. The 3D scanner 160 may use the image mask to acquire an intraoperative 3D scan of the surgical field (filtered 3D scan). The controller 110 may load medical image data (e.g., CT or MRI). The controller 110 may perform image registration between filtered intraoperative 3D scan and medical image data. The controller 110 may use optical properties to generate an image mask to include the organs of interest and exclude tissues/organs not of interest. The 3D scanner may use the image mask to acquire an intraoperative 3D scan of the surgical field (filtered 3D scan). The controller 110 may load medical image data (e.g., CT or MRI). The controller 110 may perform segmentation medical image data (e.g., CT or MRI) to isolate organs of interest (e.g., L5 of lumber spine for spine surgery). The controller 110 may reduce the image data into surface data of organ of interest (e.g. surface of L5 of lumber spine). The controller 110 may use surface data of the organ of interest to perform surface-based image registration with intraoperative 3D scan.

The controller 110 may use optical properties to generate an image mask to include the organs of interest and exclude tissues/organs not of interest. The 3D scanner 160 may use the image mask to acquire an intraoperative 3D scan of the surgical field (filtered 3D scan). The controller 110 may load medical image data (e.g., CT or MRI). The controller 110 may perform segmentation on medical image data (e.g., CT or MRI) to isolate organs of interest (e.g., L5 of lumber spine for spine surgery). The controller 110 may reduce the image data into surface data of the organ of interest (e.g., surface of L5 of lumber spine). The controller 110 may use surface data of the organ of interest to perform surface-based image registration with the intraoperative 3D scan. The tracker 130 may track positions of at least one entity in surgery. The display 120 may display surgical navigation information to the user.

In another embodiment, image mask may be constructed based on thermal properties. In one aspect thermal properties may be obtained using thermal imaging. In one embodiment, the biological tissues and surgical instruments/tools are differentiated based on thermal properties. For instance, biological tissues tend to have higher temperature compared to surgical instruments and tools. Based on the thermal properties, tissues and metal/plastics/tools may be differentiated. In another aspect, the thermal properties may be obtained using infrared imaging. Based on thermal properties of tissues, an image mask may be constructed to filter surgical tools or instruments (e.g. retractor) from the intraoperative 3D scan data. For example, an image mask may be constructed to filter surgical tools from the intraoperative 3D scan data, leaving only data from biological tissues. The filtered 3D scan data may be used for image registration and navigation, improving the registration accuracy.

The imaging detector 180 may acquire an image of thermal properties. The controller 110 may assign pixels or voxels of thermal property type 1 to passband (logical level 1). The controller 110 may assign pixels or voxels of thermal property type 2 to rejection band (logical level 0). The controller 110 may output an image mask based on thermal properties. The controller 110 may use thermal properties to generate an image mask to include the organs of interest and exclude surgical tools/instruments. The 3D scanner 160 may use the image mask to acquire an intraoperative 3D scan of the surgical field (filtered 3D scan). The controller 110 may load medical image data (e.g., CT or MRI). The controller 110 may perform image registration between filtered intraoperative 3D scan and medical image data.

The controller 110 may use thermal properties to generate an image mask to include the organs of interest and exclude surgical tools/instruments. The 3D scanner 160 may use the image mask to acquire an intraoperative 3D scan of the surgical field (filtered 3D scan). The controller 110 may load medical image data (e.g., CT or MRI). The controller 110 may perform segmentation medical image data (e.g., CT or MRI) to isolate organs of interest (e.g., L5 of lumber spine for spine surgery.) The controller 110 may reduce the image data into surface data of the organ of interest (e.g., surface of L5 of lumber spine). The controller 110 may use surface data of the organ of interest to perform surface-based image registration with intraoperative 3D scan. The tracker 130 may track positions of at least one entity in surgery. The display 120 may display surgical navigation information to the user.

In another embodiment, image mask may be constructed based on tissue properties obtained from other imaging modalities. In one aspect tissues properties may be obtained using ultrasound imaging. For example, ultrasound may be used to differentiate soft tissues from bony tissues. Either 2D ultrasound or 3D ultrasound may be used. In one example, the mask may be constructed using tissue properties. The imaging detector 180 may acquire an image of tissue properties (e.g., ultrasound image). The controller 110 may assign pixels or voxels of tissue property type 1 to passband (logical level 1). The controller 110 may assign pixels or voxels of tissue property type 2 to rejection band (logical level 0). The controller 110 may output an image mask based on tissue properties.

The controller 110 may use tissue properties to generate an image mask to include the organs of interest and exclude tissues/organs not of interest. The 3D scanner 160 may use the image mask to acquire an intraoperative 3D scan of the surgical field (filtered 3D scan). The controller 110 may load medical image data (e.g., CT or MRI). The controller 110 may perform image registration between filtered intraoperative 3D scan and medical image data. The controller 110 may use tissue properties to generate an image mask to include the organs of interest and exclude tissues/organs not of interest. The 3D scanner 160 may use the image mask to acquire an intraoperative 3D scan of the surgical field (filtered 3D scan). The controller 110 may load medical image data (e.g., CT or MRI). The controller 110 may perform segmentation medical image data (e.g., CT or MRI) to isolate the organ of interest (e.g., L5 of lumber spine for spine surgery). The controller 110 may reduce the image data into surface data of the organ of interest (e.g., surface of L5 of lumber spine). The controller 110 may use surface data of the organ of interest to perform surface-based image registration with intraoperative 3D scan. The tracker 130 may track positions of the at least one entity in surgery. The display 120 may display surgical navigation information to the user.

In another embodiment, image mask may be constructed based on machine learning and image recognition. In one aspect, tissues properties may be obtained using supervised machine learning. In another aspect, tissues properties may be obtained using unsupervised machine learning. In yet another aspect, tissues properties may be obtained using reinforcement learning. In yet another aspect, tissues properties may be obtained using artificial neural network. For example, machine learning and image recognition may be used to differentiate soft tissues from bony tissues. The controller 110 may perform machine learning for tissue classification to generate tissue class 1 and tissue class 2. The controller 110 may assign pixels or voxels of tissue class 1 to passband (logical level 1). The controller 110 may assign pixels or voxels of tissue class 2 to rejection band (logical level 0). The controller 110 may output an image mask based on machine learning.

The controller 110 may use machine learning to generate an image mask to include the organs of interest and exclude tissues/organs of interest. The 3D scanner 1607 may use the image mask to acquire an intraoperative 3D scan of the surgical field (filtered 3D scan). The controller 110 may load medical image data (e.g., CT or MRI). The controller 110 may perform image registration between filtered intraoperative 3D scan and medical image data. The controller 110 may use machine learning to generate an image mask to include the organs of interest and exclude tissues/organs not of interest. The 3D scanner 160 may use the image bask to acquire an intraoperative 3D scan of the surgical field (filtered 3D scan). The controller 110 may load medical image data (e.g., CT or MRI). The controller 110 may perform segmentation medical image data (e.g., CT or MRI) to isolate the organ of interest (e.g., L5 of lumber spine for spine surgery). The controller 110 may reduce the image data into surface data of organ of interest (e.g., surface of L5 of lumber spine). The controller 110 may use surface data of the organ of interest to perform surface-based image registration with intraoperative 3D scan. The tracker 130 may track positons of at least one entity in surgery. The display 120 may display surgical navigation information to the user.

Integration with Other Surgical Navigation and Robotic Surgery Systems

In one embodiment, a surgical imaging and navigation system FIG. 10 comprises a controller 1010, a 3D scanning controller 150, a 3D scanner 160, an intraoperative imaging controller 170, an imaging detector 180, and communication interface 1080. The 3D scanning controller 150 controls the modes and properties of 3D scanner 160. For instance, the size of the area of 3D scanning, the resolution of 3D scanning, the speed of 3D scanning, the timing of 3D scanning may be controlled by the 3D scanning controller 150. The intraoperative imaging controller 170 controls the modes and properties of imaging detector 180. For instance, the size of the area of intraoperative imaging, the resolution of intraoperative imaging, the speed of intraoperative imaging, the timing of intraoperative imaging, and the mode of intraoperative imaging may be controlled by the intraoperative imaging controller 170. The communication interface 1080 communicates with other surgical navigation systems. In one example, the image registration calculated using the surgical imaging and navigation system 1000 may be communicated to another surgical navigation system via the communication interface 1080. The communication interface 1080 may be either wired or wireless. The controller 1010 is in in operative communication with the 3D scanning controller 150, intraoperative imaging controller 170, and the communication interface 1080. The controller 1010 can run software such as image registration software or computer vision algorithms to enable surgical navigation and communicate the image registration to another surgical navigation system. Other surgical navigation system can have different functionalities, such as intraoperative CT scan, 3D fluoroscopy, optical tracking, or electromagnetic tracking, etc.

With an exemplary system previously discussed, a method for surgical imaging and navigation may be implemented to provide intraoperative guidance to surgeons and other medical professionals. The 3D scanner 160 may capture a 3D scan of anatomy of a patient. The controller 1010 may load medical image data (e.g., CT or MRI). The controller 1010 may perform segmentation on medical image data (e.g., CT or MRI) to isolate organ of interest (e.g., L5 of lumber spine for spine surgery). The controller 1010 may reduce the image data into surface data of organ of interest (e.g., surface of L5 of lumber spine). The controller 1010 may perform surface-based image registration between the surface data of the organ of interest and the intraoperative 3D scan. The communications interface 1080 may communicate the image registration to another surgical navigation system.

CONCLUSION

It is to be appreciated that the Detailed Description section, and not the Abstract section, is intended to be used to interpret the claims. The Abstract section may set forth one or more, but not all exemplary embodiments, of the present disclosure, and thus, is not intended to limit the present disclosure and the appended claims in any way.

The present disclosure has been described above with the aid of functional building blocks illustrating the implementation of specified functions and relationships thereof. The boundaries of these functional building blocks have been arbitrarily defined herein for the convenience of the description. Alternate boundaries may be defined so long as the specified functions and relationships thereof are appropriately performed.

It will be apparent to those skilled in the relevant art(s) the various changes in form and detail may be made without departing from the spirt and scope of the present disclosure. Thus the present disclosure should not be limited by any of the above-described exemplary embodiments, but should be defined only in accordance with the following claims and their equivalents.

What is claimed is:

1. A system for executing a three-dimensional (3D) intraoperative scan of a patient to generate a plurality of intraoperative images of the patient that enables a surgeon to navigate during a surgical operation on the patient, comprising: a 3D scanner that includes a projector, an image sensor, and a non-statistical projection pattern generator, wherein:

the non-statistical projection pattern generator is configured to generate a plurality of non-statistical patterns with each non-statistical pattern including a plurality of identified characteristics, wherein each plurality of identified characteristics associated with each non-statistical pattern are different variations of each other, the projector is configured to project each non-statistical pattern as generated by the non-statistical projection pattern generator onto the patient in series, wherein each variation in the identified characteristics of each non-statistical pattern as projected onto the patient is adjusted based on when in the series each corresponding non-statistical pattern is projected onto the patient, and the image sensor is configured to capture a two-dimensional (2D) intraoperative image of a plurality of object points associated with the patient after each non-statistical pattern as generated by the non-statistical projection pattern generator is projected onto the patient;

a 3D scanning controller that includes at least one processor and a memory coupled with the processor, the memory including instructions that when executed by the processor cause the processor to:

identify a position of each object point associated with the patient that is captured by the image sensor after each non-statistical pattern as generated by the non-statistical pattern generator is projected onto the patient, determine an actual position of each object point after the plurality of non-statistical patterns as generated by the non-statistical pattern generator is projected onto the patient based on an average position of each object point determined from each identified position of each object point as generated after each non-statistical pattern as generated by the non-statistical pattern generator is projected onto the patient, and convert the 2D intraoperative image to the 3D intraoperative scan of the patient based on the actual position of each object point after the plurality of statistical patterns as generated by the non-statistical pattern generator is projected onto the patient; and a controller that includes at least one processor and a memory coupled with the processor, the memory including instructions that when executed by the processor cause the processor to:

co-register pre-operative image data captured from at least one pre-operative image of the patient with intraoperative image data provided by the 3D intraoperative scan as generated based on the non-statistical pattern projected onto the patient and converted into the 3D intraoperative scan by 3D scanning controller, and instruct a display to display the co-registered pre-operative image data as captured from the at least one pre-operative image with the intraoperative image data provided by the 3D intraoperative scan as the surgeon navigates during the surgical operation as the 3D intraoperative scan is generated based on the non-statistical pattern projected onto the patient and converted into the 3D intraoperative scan by the 3D scanning controller.

2. The system of claim 1, wherein the non-statistical projection pattern generator is further configured to generate the plurality of non-statistical patterns with each non-statistical pattern being a variation in scale from each other non-statistical pattern that is projected onto the patient.

3. The system of claim 2, wherein the non-statistical projection pattern generator is further configured to:

generate a first non-statistical pattern that includes a stripe with a resolution that is decreased to a resolution that the projector is capable to project and the image sensor is capable to capture; and generate each additional non-statistical pattern that includes a stripe being an increased variation in scale from the first non-statistical pattern and each additional non-statistical pattern is a variation from each other additional non-statistical pattern in the resolution of each stripe associated with each additional non-statistical pattern.

4. The system of claim 3, wherein the projector is further configured to:

project each non-statistical pattern that varies in resolution to each corresponding horizontal row of pixels included in the 2D intraoperative image captured by the image sensor; and project each non-statistical pattern that varies in resolution to each corresponding vertical column of pixels included in the 2D intraoperative image captured by the image sensor.

5. The system of claim 1, wherein the 3D scanning controller is further configured to:

determine each depth of each object point as captured in the 2D intraoperative image by the image sensor of the patient based on a depth associated with each pixel included in the 2D intraoperative image that is determined after each non-statistical pattern is projected onto the patient; and convert the 2D intraoperative image to the 3D intraoperative scan of the patient based on the depth of each object point as determined after the plurality of statistical patterns is projected onto the patient.

6. The system of claim 1, wherein the 3D scanning controller is further configured to:

determine a plurality of first epipolar lines associated with a projection image plane of the projection of the plurality of non-statistical patterns and a plurality of second epipolar lines associated with a 2D intraoperative image plane of the captured 2D intraoperative image based on an epipolar plane that triangulates the plurality of object points generated when each non-statistical pattern is applied to the 2D intraoperative image to the plurality of object points included in the 2D intraoperative, wherein each epipolar line provides a depth of each object point as projected from the projection image plane associated with the projector and the 2D intraoperative image plane associated with the 2D intraoperative image; and convert the 2D intraoperative image to the 3D intraoperative scan of the patient based on the depth of each object point provided by each corresponding epipolar line.

* * * * *